United States Patent
Schweinsberg et al.

(10) Patent No.: US 8,784,507 B2
(45) Date of Patent: Jul. 22, 2014

(54) POST OXIDATIVE HAIR TREATMENT AGENT WITH SILICONE

(71) Applicant: Henkel AG & Co. KGaA, Duesseldorf (DE)

(72) Inventors: Matthias Schweinsberg, Hamburg (DE); Jisook Baek, Hamburg (DE); Astrid Kleen, Hamburg (DE); Erik Schulze zur Wiesche, Hamburg (DE); Antje Gebert, Duesseldorf (DE); Monika Nebel, Norderstedt (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 14/132,184

(22) Filed: Dec. 18, 2013

(65) Prior Publication Data

US 2014/0170223 A1    Jun. 19, 2014

(30) Foreign Application Priority Data

Dec. 19, 2012   (DE) .......................... 10 2012 223 807

(51) Int. Cl.
    *A61Q 5/10*    (2006.01)
    *A61Q 5/00*    (2006.01)
    *A61K 8/898*   (2006.01)

(52) U.S. Cl.
    CPC .. *A61Q 5/10* (2013.01); *A61Q 5/00* (2013.01); *A61K 8/898* (2013.01)
    USPC ....................................... 8/405; 8/406; 8/581

(58) Field of Classification Search
    CPC ............ A61Q 5/00; A61Q 5/10; A61K 8/898
    USPC .............................................. 8/405, 406, 581
    See application file for complete search history.

(56) References Cited

U.S. PATENT DOCUMENTS

| 6,824,765 B2 * | 11/2004 | Gawtrey et al. ............... 424/70.1 |
| 7,220,408 B2 | 5/2007 | Decoster et al. |
| 7,223,385 B2 | 5/2007 | Gawtrey et al. |
| 7,485,289 B2 | 2/2009 | Gawtrey et al. |
| 7,504,094 B2 | 3/2009 | Decoster et al. |

FOREIGN PATENT DOCUMENTS

| AU | 2005256329 B2 | 1/2006 |
| DE | 19756454 C1 | 6/1999 |

OTHER PUBLICATIONS

STIC Search Report dated Feb. 10, 2014.*

* cited by examiner

*Primary Examiner* — Eisa Elhilo
(74) *Attorney, Agent, or Firm* — David K. Benson

(57) ABSTRACT

A method for oxidative lightening and/or coloring of keratinic fibers include:
  a) a coloring and/or lightening agent applied onto the keratinic fibers, which agent is obtained by mixing a composition (A) that contains at least one alkalizing agent with a composition (B) that contains, in a cosmetic carrier, at least one oxidizing agent,
  b) subsequently, within a time span from about one second to about 24 hours after step a), a post-treatment agent that contains at least one 4-morpholinomethyl-substituted silicone of formula (V), applied onto the keratinic fibers, in particular onto the hair.

11 Claims, No Drawings

POST OXIDATIVE HAIR TREATMENT AGENT WITH SILICONE

CROSS REFERENCE TO RELATED APPLICATION

This application claims priority to German Patent Application No. DE 10 2012 223 807.7, filed Dec. 19, 2012, its contents hereby incorporated in its entirety.

TECHNICAL FIELD

The present invention relates to a low-impact method for oxidative lightening and/or coloring of keratinic fibers, in particular of hair, in which oxidizing influences on the keratinic fibers are mitigated.

BACKGROUND

In the context of oxidative coloring and also oxidative lightening of hair, the problem arises that irritation of the scalp and damage to the keratinic fibers can occur as a result of the aggressive agents. In particular, the natural hydrophobicity of the keratinic fibers is reduced because the coloring agents resp. lightening agents must first make the hair capable of penetration in order to exert their effect. The water-repellent effect on the one hand, however, provides natural protection for the hair; on the other hand, parameters desired by the consumer, such as shine, softness, suppleness, and the "drape" of the hair, are closely linked to it.

In order to overcome the aforesaid disadvantages, so-called post-treatment agents that are intended to compensate for hair damage caused by the oxidizing agent are on the market. These often make the hair heavy, however, or negatively affect the outcome of the previously performed lightening resp. coloring of the hair; in particular, the washing fastness of the color can be degraded by the post-treatment agent.

An object of the present invention is to make available a method for oxidative hair treatment, with a hair-protecting post-treatment, that overcomes the aforesaid disadvantages without counteracting the success of a previously performed oxidative hair treatment. The intention is in particular to make available a method in which the hair is not made heavier, and in which the desired effect can also be achieved in the context of a post-treatment not occurring immediately after the oxidative hair treatment, with the result that the time span between oxidative hair treatment and post-treatment can be extended.

DETAILED DESCRIPTION

The use of aminated silicones in hair care is established art. They are widely used in shampoos and in particular in conditioners in order to exert care-providing effects therein. EP 1771144 B1, for example, discloses hair-conditioning agents having aminofunctional silicones. The agents described therein are post-treatment agents.

European patents EP 1312334 B1 (aminosilicone and thickener) and EP 1312335 B1 (aminosilicone and conditioner) also disclose hair post-treatment agents.

It has now been found that a post-treatment of the keratinic fibers with special 4-morpholinomethyl-substituted silicones within a specific time period after an oxidative hair treatment results in an appreciable reduction in hair damage. A "reduction in hair damage" is to be understood for purposes herein in particular to mean that the structure of the keratinic fibers, in particular of the hair, is less intensely attacked by the oxidizing agent, so that in particular the surface of the fibers resp. of the hair becomes less roughened, the hair ends experience less splitting, and/or less hair breakage occurs. In addition, particularly good color results are also achieved, especially colors having a high level of washing fastness.

The subject matter of the present invention is, in a first embodiment, a method for oxidative lightening and/or coloring of keratinic fibers, in particular of hair, in which a) a coloring and/or lightening agent is applied onto the keratinic fibers, which agent is obtained by mixing a composition (A) that contains at least one alkalizing agent with a composition (B) that contains, in a cosmetic carrier, at least one oxidizing agent, b) subsequently, within a time span from one second to 24 hours after step a), a post-treatment agent that contains at least one 4-morpholinomethyl-substituted silicone of formula (V),

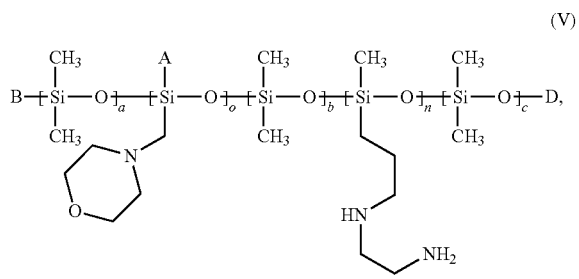

in which
A denotes a structural unit (I), (II), or (III) bound via —O—

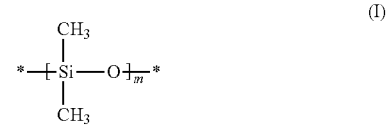

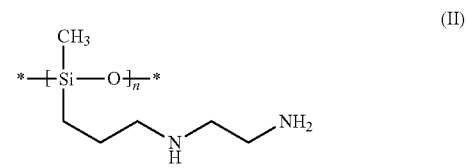

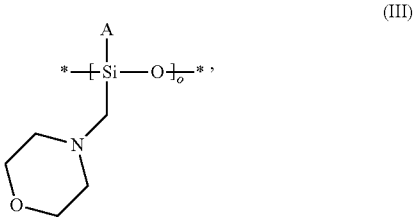

or an oligomeric or polymeric residue bound via —O— containing structural units of formulas (I), (II), or (III), or half of an oxygen atom connecting to a structural unit (III), or denotes —OH,

* denotes a bond to one of the structural units (I), (II), or (III), or denotes a terminal group B (Si-bound) or D (O-bound), B denotes an —OH, —O—Si(CH₃)₃, —O—Si(CH₃)₂OH, —O—Si(CH₃)₂OCH₃ group, D denotes an —H, —Si(CH₃)₃, —Si(CH₃)₂OH, —Si(CH₃)₂OCH₃ group, a, b, and c denote integers from 0 to 990, with the provision that a+b+c>0, m, n, and o denote integers from 1 to 990, is applied onto the keratinic fibers, in particular onto the hair.

Post-treatment agents preferably used according to the present invention are characterized in that they contain the at least one 4-morpholinomethyl-substituted silicone of formula (V), which comprises respectively at least one of the structural units of formulas (I), (II), and (III), in a total quantity from about 0.001 to about 5 wt %, preferably about 0.005 to about 2 wt %, particularly preferably about 0.01 to about 1 wt %, extraordinarily preferably about 0.02 to about 0.1 wt %, based in each case on the total weight of the post-treatment agent.

Post-treatment agents preferably used according to the present invention are characterized in that they contain the at least one 4-morpholinomethyl-substituted silicone of formula (V) in a form emulsified in water. Post-treatment agents used particularly preferably contain about 30 to about 98 wt %, preferably about 40 to about 90 wt %, particularly preferably about 50 to about 85 wt %, extraordinarily preferably about 60 to about 80 wt % water, based in each case on the total weight of the post-treatment agent.

Post-treatment agents used particularly preferably are present in the form of an oil-in-water emulsion in which the number-average size of the silicone particles in the emulsion is in the range from about 3 to about 500 nm, preferably in the range from about 5 to about 60 nm.

Structural units of formulas (I), (II), and (III) can be present statistically distributed in the molecule, but the silicones used according to the present invention can also be block copolymers made up of blocks of the individual structural units, in which context the blocks can in turn be present in statistically distributed fashion.

The * on the free valences of structural units (I), (II), or (III) denotes a bond to one of the structural units (I), (II), or (III) or a terminal group B (Si-bound) or D (O-bound).

The silicones used according to the present invention can be trimethylsilyl-terminated at both ends (D=—Si(CH₃)₃, B=—O—Si(CH₃)₃), but they can also be dimethylsilylhydroxy- or dimethylsilylmethoxy-terminated at one or two ends. Silicones used particularly preferably in the context of the present invention have at least one terminal dimethylsilylhydroxy group, i.e. are selected from silicones in which B=—O—Si(CH₃)₂OH and D=—Si(CH₃)₃
B=—O—Si(CH₃)₂OH and D=—Si(CH₃)₂OH
B=—O—Si(CH₃)₂OH and D=—Si(CH₃)₂OCH₃
B=—O—Si(CH₃)₃ and D=—Si(CH₃)₂OH
B=—O—Si(CH₃)₂OCH₃ and D=—Si(CH₃)₂OH.

These silicones result in exorbitant improvements in the hair properties of the hair treated in accordance with the method according to the present invention, in particular in a tremendous decrease in contact angle and in smoothing of the hair surface.

In structural unit (III), residue A can denote
a structural unit (I), (II), or (III) bound via —O—, or
an oligomeric or polymeric residue bound via —O— containing structural units of formulas (I), (II), and (III), or half of an oxygen atom connecting to a structural unit (III), or can denote —OH.

In the first case, structural unit (III) becomes one of the structural units (IIIa), (IIIb), or (IIIc):

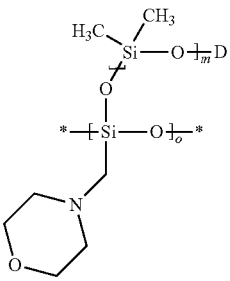
(IIIa)

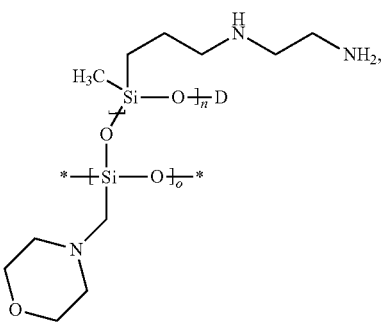
(IIIb)

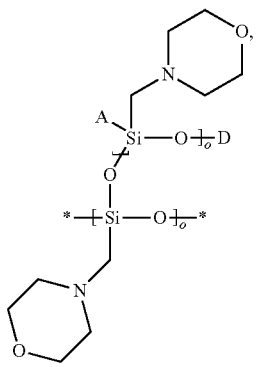
(IIIc)

where m=n=o=1, and A resp. D are as defined above.

In the second case, in the formulas (IIIa), (IIIb), and (IIIc) recited above the indices m, n, and o can denote integers from 2 to 990. The second case also, however, covers oligomeric or polymeric residues that contain at least two different structural units of formulas (I), (II), or (III), as depicted in formula (IIId):

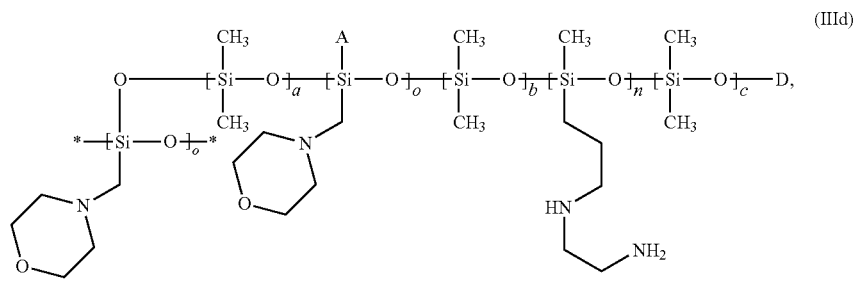

(IIId)

in which a, b, and c denote integers from 0 to 990, with the provision that a+b+c>0, and n and o denote integers from 1 to 990.

In the third case, A denotes half of an oxygen atom connecting to a structural unit (III) (depicted in structural unit (IIIe)) or denotes —OH (depicted in structural unit (IIIf))

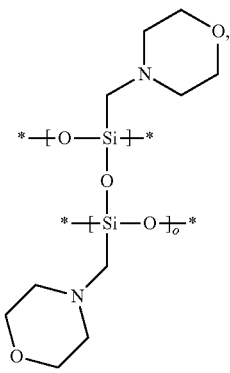

(IIIe)

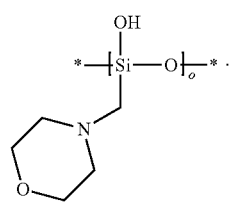

(IIf)

As already mentioned, the structural units of formulas (I), (II), and (III) can preferably be present in statistically distributed fashion. Post-treatment agents preferably used according to the present invention contain at least one 4-morpholinomethyl-substituted silicone of formula (V)

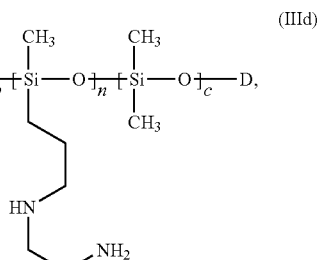

(V)

in which

A denotes a structural unit (I), (II), or (III) bound via —O—, or an oligomeric or polymeric residue bound via —O— containing structural units of formulas (I), (II), or (III), or half of an oxygen atom connecting to a structural unit (III), or denotes —OH, B denotes an —OH, —O—Si(CH$_3$)$_3$, —O—Si(CH$_3$)$_2$OH, —O—Si(CH$_3$)$_2$OCH$_3$ group, D denotes an —H, —Si(CH$_3$)$_3$, —Si(CH$_3$)$_2$OH, —Si(CH$_3$)$_2$OCH$_3$ group, a, b, and c denote integers from 0 to 990, with the provision that a+b+c>0, n, and o denote integers from 1 to 990.

Structural formula (V) is intended to illustrate the fact that the siloxane groups n and o do not obligatorily need to be bound directly to an end grouping B resp. D. Instead, in preferred formulas (V) a>0 or b>0, and in particularly preferred formulas (V) a>0 and b>0, i.e. the terminal grouping B resp. D is preferably bound to a dimethylsiloxy grouping. In formula (V) as well, the siloxane units a, b, c, n, and o are preferably statistically distributed.

The silicones represented by formula (V) and used according to the present invention can also be trimethylsilyl-terminated at both ends (D=—Si(CH$_3$)$_3$, B=—O—Si(CH$_3$)$_3$), but they can also be dimethylsilylhydroxy- or dimethylsilylmethoxy-terminated at one or two ends. Silicones used particularly preferably in the context of the present invention have at least one terminal dimethylsilylhydroxy group, i.e. are selected from silicones in which B=—O—Si(CH$_3$)$_2$OH and D=—Si(CH$_3$)$_3$ B=—O—Si(CH$_3$)$_2$OH and D=—Si(CH$_3$)$_2$OH B=—O—Si(CH$_3$)$_2$OH and D=—Si(CH$_3$)$_2$OCH$_3$ B=—O—Si(CH$_3$)$_3$ and D=—Si(CH$_3$)$_2$OH B=—O—Si(CH$_3$)$_2$OCH$_3$ and D=—Si(CH$_3$)$_2$OH.

These 4-morpholinomethyl-substituted silicones of formula (V), which respectively comprise at least one of the structural units of formulas (I), (II), and (III), result in surprisingly large improvements in the hair properties of the hair treated in accordance with the method according to the present invention, in particular in tremendously improved hair protection and color protection in the context of oxidative hair coloring.

In formula (V) as well, residue A can denote
- a structural unit (I), (II), or (III) bound via —O—, or
- an oligomeric or polymeric residue bound via —O— containing structural units of formulas (I), (II), and (III), or
- half of an oxygen atom connecting to a structural unit (III), or can denote —OH.

By analogy with the statements regarding structural unit (III), formula (V) is thus refined to one of formulas (Va), (Vb), (Vc), (Vd,), (Ve), or (Vf):

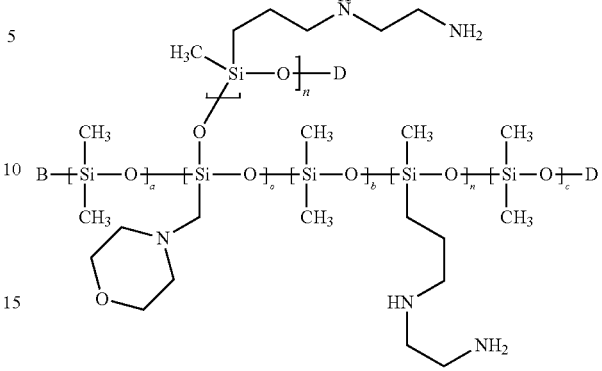
(Vb)

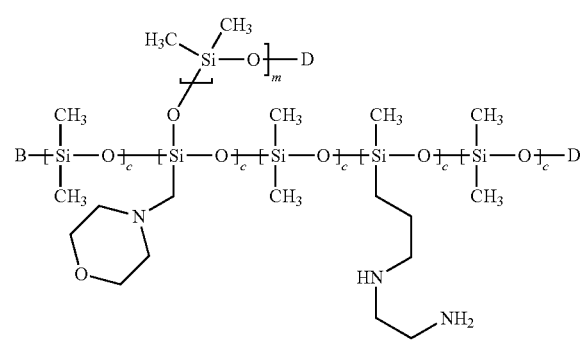
(Va)

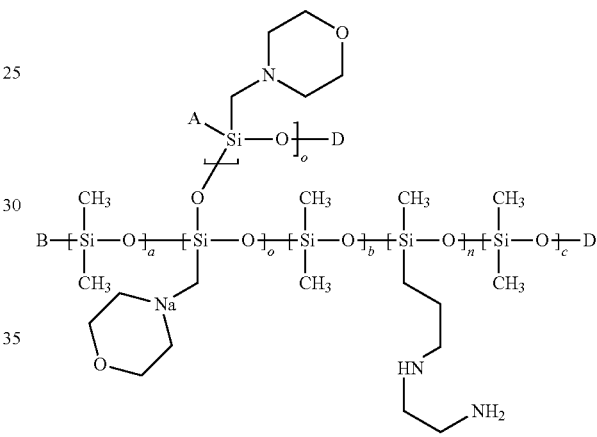
(Vc)

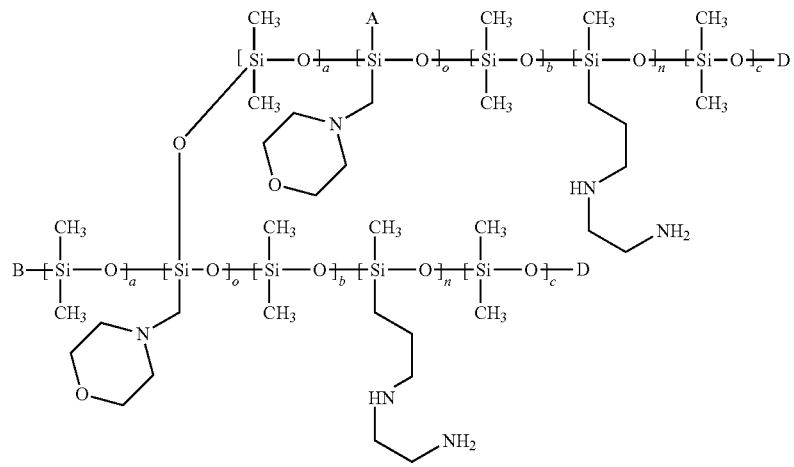
(Vd)

(Ve)

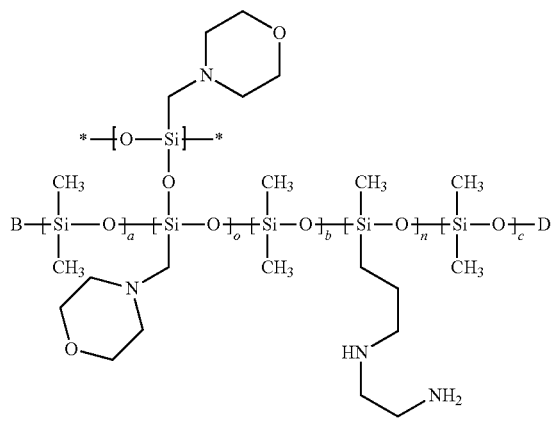

(Vf)

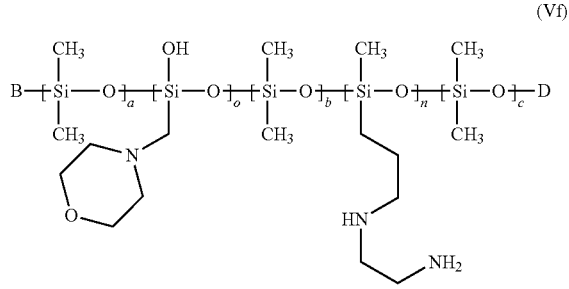

Structural unit (III) resp. the siloxane units o in formulas (V) can, via group A, constitute nest structures resp. partial cage structures when A denotes half of an oxygen atom connecting to a structural unit (III). Post-treatment agents according to the present invention that contain silicones having corresponding 4-morpholinomethyl-substituted silsesquioxane substructures are preferred according to the present invention, since these silicones result in enormously improved hair protection in the context of oxidative hair treatment.

Post-treatment agents preferably used according to the present invention are characterized in that they contain at least one 4-morpholinomethyl-substituted silicone that comprises structural units of formula (VI)

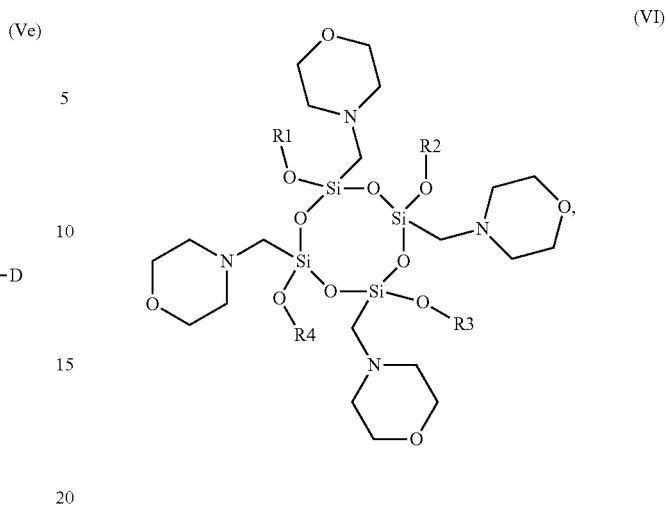

in which

R1, R2, R3, and R4 mutually independently denote —H, —CH$_3$, a group D, a structural unit (I), (II), or (III), or an oligomeric or polymeric residue containing structural units of formulas (I), (II), or (III), or two of the residues R1, R2, R3, and R4 denote a structural unit —Si(R6)(R5)-, where R5=—CH$_3$ or a structural unit of formula (I) or (II) or (III) or an oligomeric or polymeric residue containing structural units of formulas (I), (II), or (III), R6=—OH, —CH$_3$, or a structural unit of formula (I) or (II) or (III) or an oligomeric or polymeric residue containing structural units of formulas (I), (II), or (III).

In preferred silicones of formula (VI), at least one of the residues R1, R2, R3, or R4 denotes an oligomeric or polymeric residue containing structural units of formulas (I), (II), or (III).

In further preferred silicones of formula (VI), at least one of the residues R1, R2, R3, or R4 denotes an oligomeric or polymeric residue containing structural units of formulas (I) and (II).

In even further preferred silicones of formula (VI), at least one of the residues R1, R2, R3, or R4 denotes an oligomeric or polymeric residue containing structural units of formulas (I) and (II) and (III).

At least one of the residues R1, R2, R3, or R4 preferably denotes an [—Si(CH$_3$)$_2$—O]$_m$ grouping, i.e. an oligomer resp. polymer of structural unit (I). In addition, preferably structural unit (II) resp. an oligomer or polymer thereof is never bound in the molecule alone, but instead always in a statistical distribution with further structural units of formula (I) as one of the residues R1, R2, R3, or R4.

Preferred silicones of formula (VI) can be described by formula (VI a)

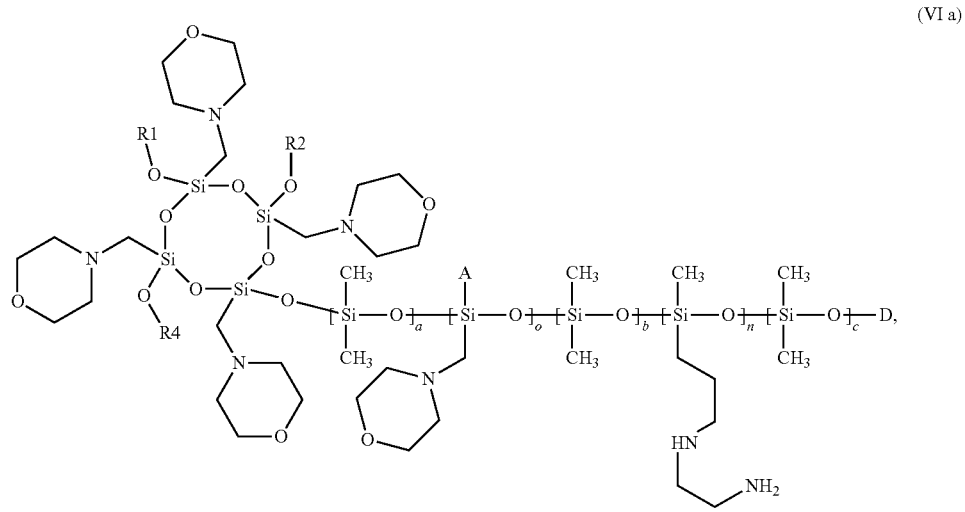

(VI a)

in which

R1, R2, and R4 mutually independently denote —H, —CH₃, a group D, a structural unit (I), (II), or (III), or an oligomeric or polymeric residue containing structural units of formulas (I), (II), or (III), or two of the residues R1, R2, and R4 denote a structural unit —Si(R6)(R5)-, where R5=—CH₃ or a structural unit of formula (I) or (II) or (III) or an oligomeric or polymeric residue containing structural units of formulas (I), (II), or (III), R6=—OH, —CH₃, or a structural unit of formula (I) or (II) or (III) or an oligomeric or polymeric residue containing structural units of formulas (I), (II), or (III), A denotes a structural unit (I), (II), or (III) bound via —O—, or an oligomeric or polymeric residue bound via —O— containing structural units of formulas (I), (II), or (III), or half of an oxygen atom connecting to a structural unit (III), or denotes —OH, D denotes an —H, —Si(CH₃)₃, —Si(CH₃)₂OH, —Si(CH₃)₂OCH₃ group, a, b, and c denote integers from 0 to 990, with the provision that a+b+c>0, n, and o denote integers from 1 to 990.

Further preferred silicones of formula (VI) can be described by formula (VI b)

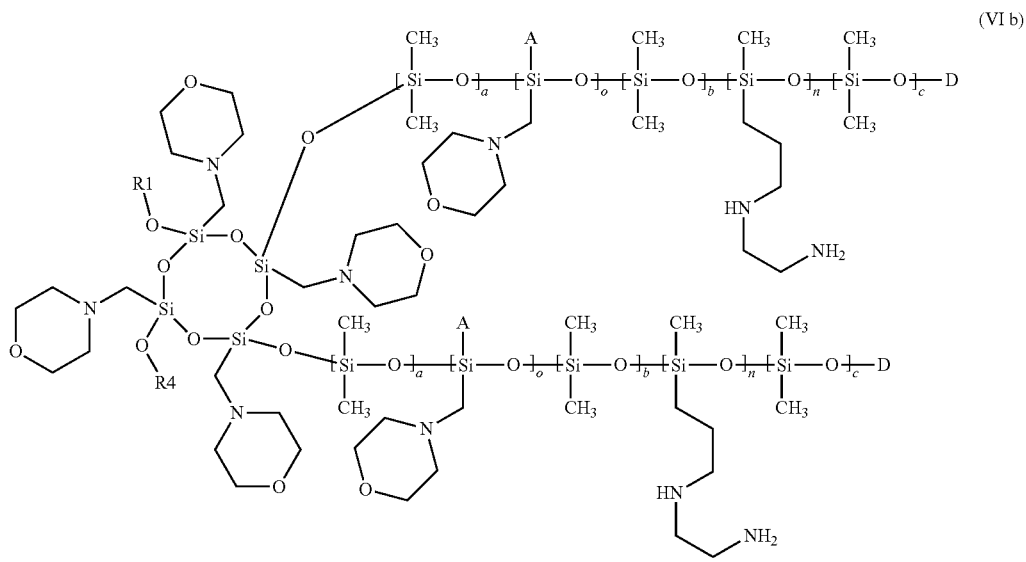

(VI b)

in which the residues and indices are as defined above.

Particularly preferred silicones of formula (VI) can be described by formula (VI c)

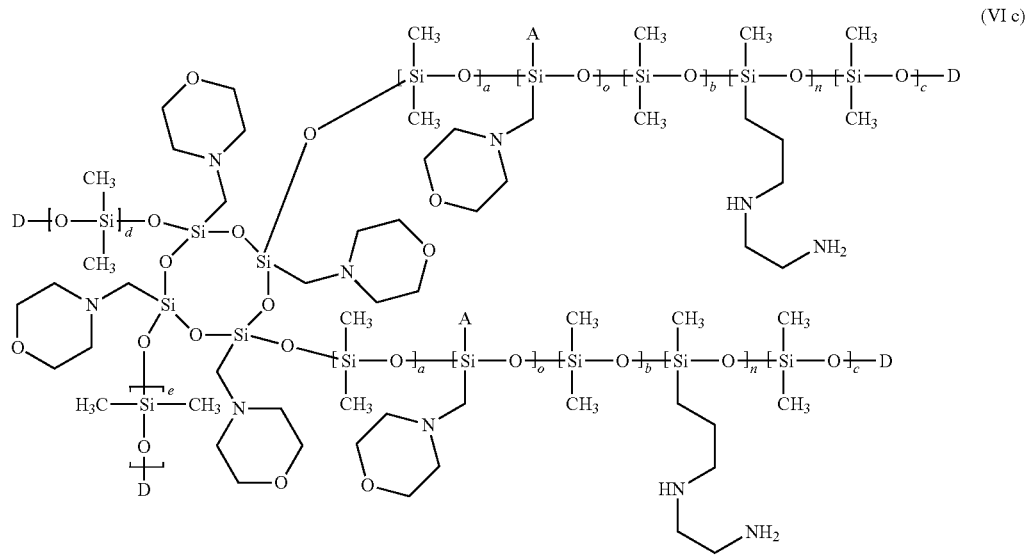

(VI c)

in which the residues and indices are as defined above, and the indices d and e denote integers from 0 to 990.

In formulas (VI a), (VI b), and (VI c), at least one of the groupings D preferably denotes —Si(CH$_3$)$_2$OH.

The silsesquioxane structures can be even more pronounced in the 4-morpholinomethyl-substituted silicones used according to the present invention, which intensifies the advantageous effects.

Particularly preferred post-treatment agents used according to the present invention are characterized in that they contain at least one 4-morpholinomethyl-substituted silicone that comprises structural units of formula (VII)

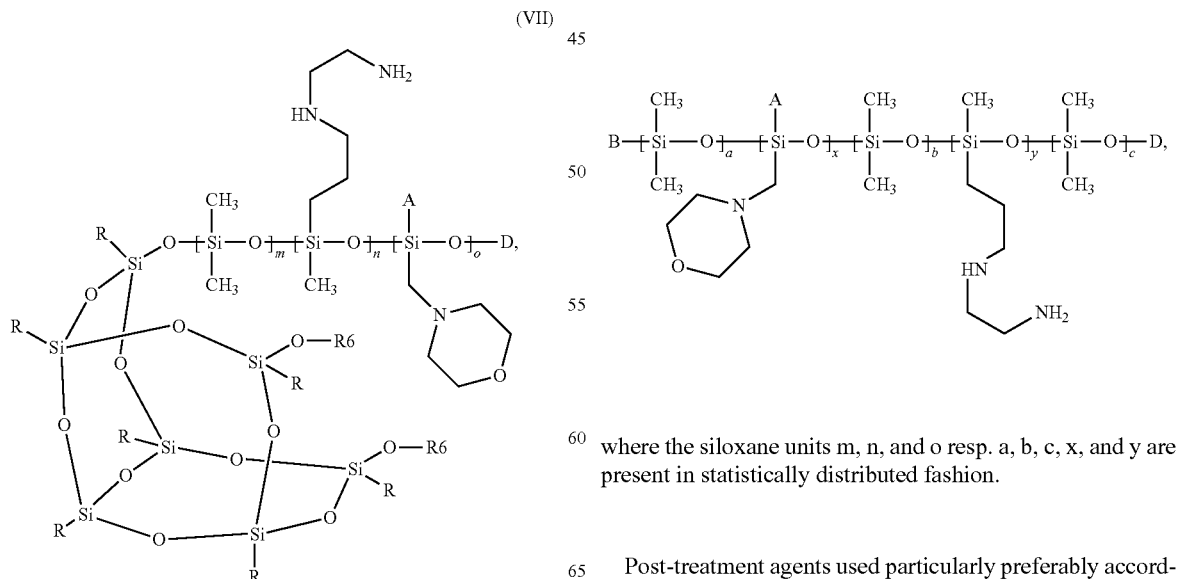

(VII)

in which

A denotes a structural unit (I), (II), or (III) bound via —O—, or an oligomeric or polymeric residue bound via —O— containing structural units of formulas (I), (II), or (III), or half of an oxygen atom connecting to a structural unit (III), or denotes —OH, D denotes an —H, —Si(CH$_3$)$_3$, —Si(CH$_3$)$_2$OH, —Si(CH$_3$)$_2$OCH$_3$ group, R denotes a 4-morpholinomethyl residue, R6 denotes —H or the grouping where the siloxane units m, n, and o resp. a, b, c, x, and y are present in statistically distributed fashion.

Post-treatment agents used particularly preferably according to the present invention contain at least one silicone of the following formula (VII a)

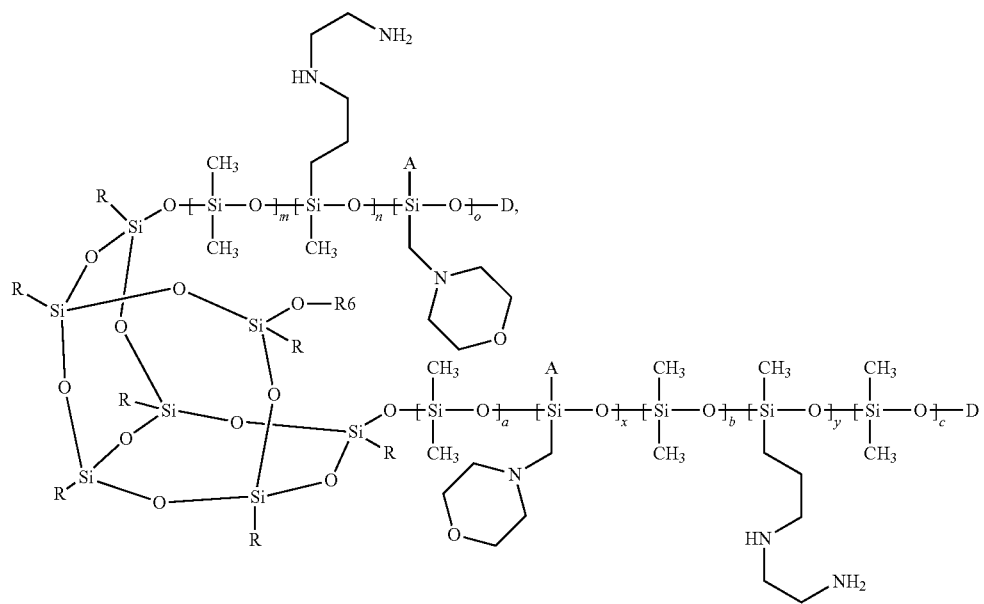
with the definitions as for formula (VII).
Very particularly preferred post-treatment agents used according to the present invention contain at least one silicone of the following formula (VII b)
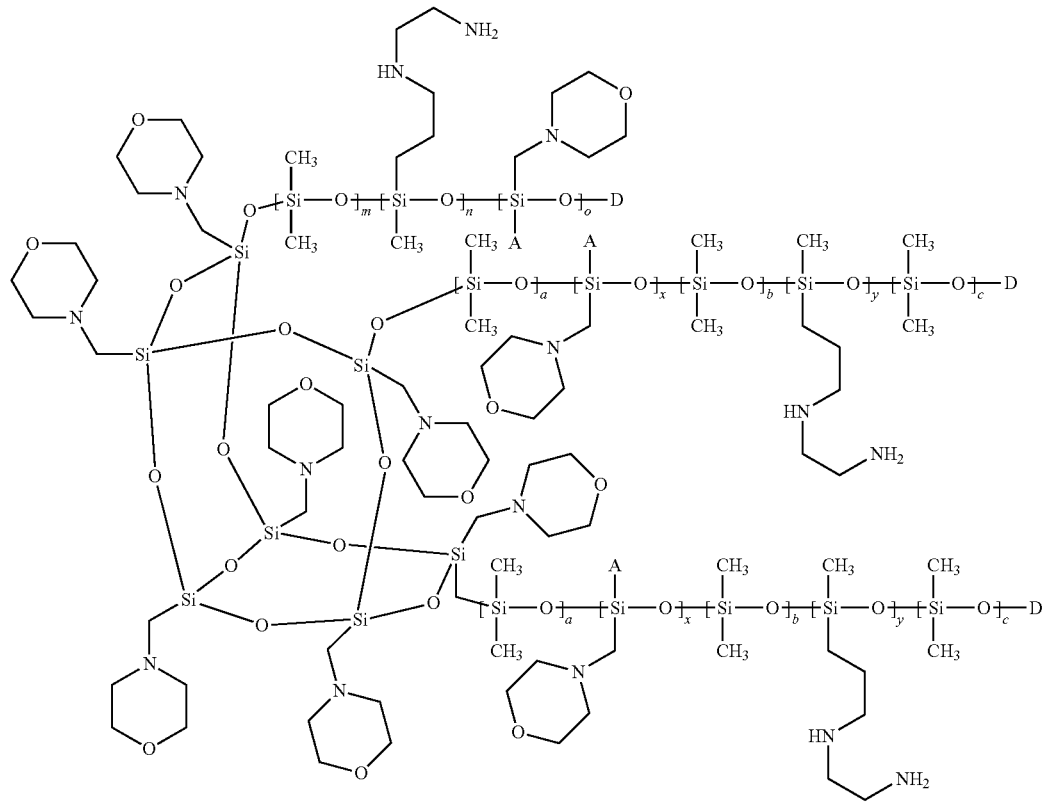
(VII b)
with the definitions as for formula (VII).

In formulas (VII), (VII a), and (VII b), the bridging oxygen atoms between the morpholinomethyl-substituted silicon atoms can also be supplemented by an —[—Si(CH$_3$)$_2$—O]$_m$ grouping, i.e. an oligomer or polymer of structural unit (I). Corresponding post-treatment agents used according to the present invention are those which contain at least one 4-morpholinomethyl-substituted silicone that comprises structural units of formula (VIII)

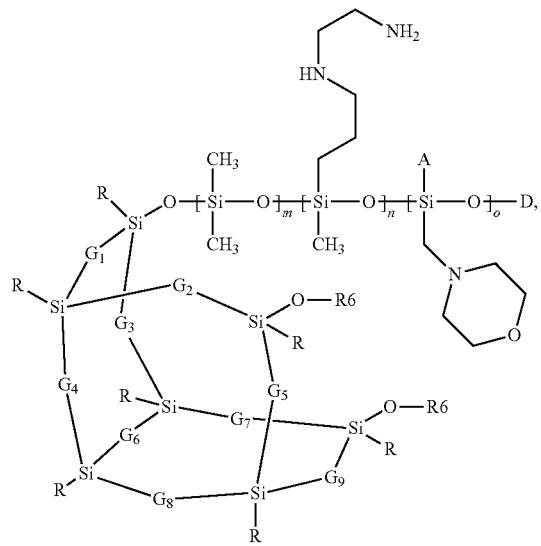

(VIII)

in which

A denotes a structural unit (I), (II), or (III) bound via —O—, or an oligomeric or polymeric residue bound via —O— containing structural units of formulas (I), (II), or (III), or half of an oxygen atom connecting to a structural unit (III), or denotes —OH, D denotes an —H, —Si(CH$_3$)$_3$, —Si(CH$_3$)$_2$OH, —Si(CH$_3$)$_2$OCH$_3$ group, G1 to G9 mutually independently denote —O— or an —[—Si(CH$_3$)$_2$—O]$_m$ group where m=1 to 200, R denotes a 4-morpholinomethyl residue, R6 denotes —H or the grouping

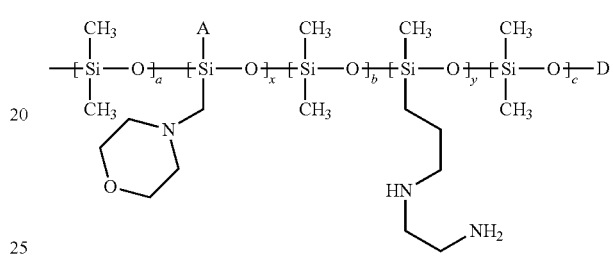

where the siloxane units m, n, and o resp. a, b, c, x, and y are present in statistically distributed fashion.

Particularly preferred post-treatment agents used according to the present invention contain at least one silicone of the following formula (VIII a)

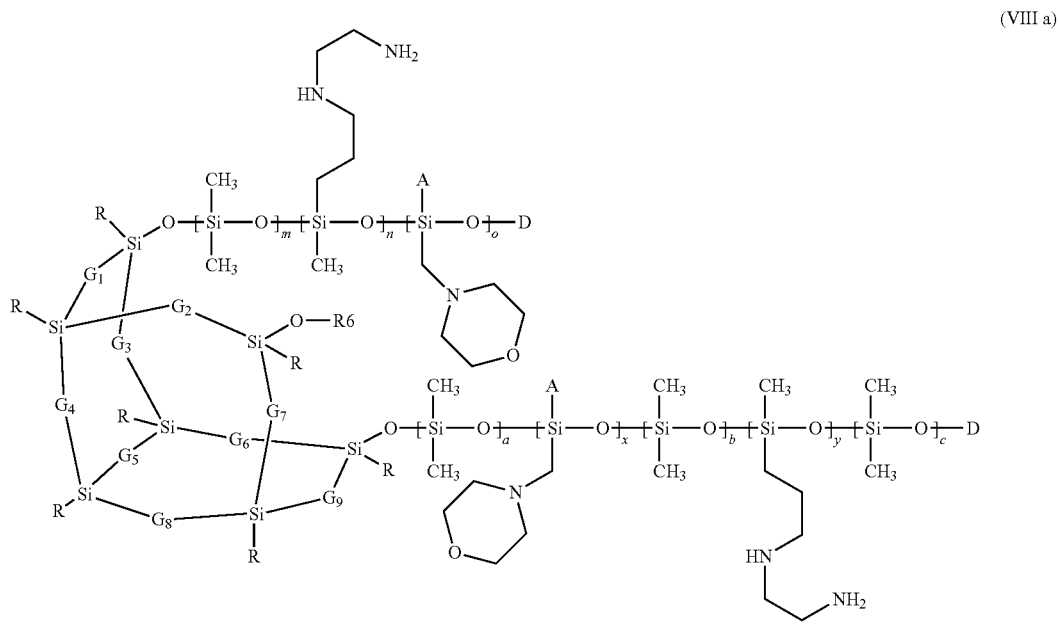

(VIII a)

with the definitions as for formula (VIII).

Very particularly preferred post-treatment agents used according to the present invention contain at least one silicone of the following formula (VIII b)

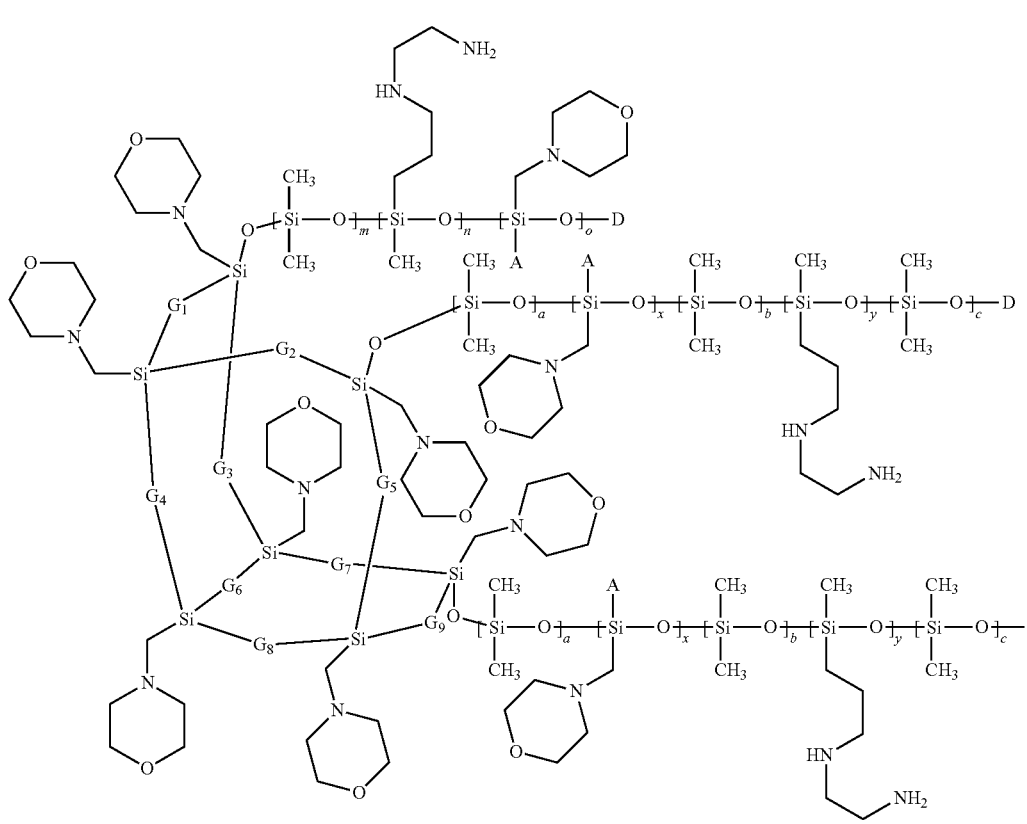

(VIIIb)

with the definitions as for formula (VIII).

Regardless of which special 4-morpholinomethyl-substituted silicone is contained in the post-treatment agents used according to the present invention, post-treatment agents that contain a 4-morpholinomethyl-substituted silicone in which more than 50 mol % of the structural units are dimethylsiloxy units, i.e. in which structural unit (I) makes up at least half of all structural units of the silicone used, are preferred for the method according to the present invention.

In other words, silicones in which $m>(n+o)$ resp. $(a+b+c)>(n+o)$, are preferred.

Even further preferred post-treatment agents used according to the present invention contain a 4-morpholinomethyl-substituted silicone in which more than 87.5 mol % of the structural units are dimethylsiloxy units, i.e. in which structural unit (I) makes up more than 875 thousandths of all structural units of the silicone used.

In other words, silicones in which $m>8(n+o)$ resp. $(a+b+c)>8(n+o)$, are preferred.

Even further preferred post-treatment agents used according to the present invention contain a 4-morpholinomethyl-substituted silicone in which more than 96 mol % of the structural units are dimethylsiloxy units, i.e. in which structural unit (I) makes at least ninety-six hundredths of all structural units of the silicone used.

In other words, silicones in which $m>25(n+o)$ resp. $(a+b+c)>25(n+o)$, are preferred.

Even further preferred post-treatment agents used according to the present invention contain a 4-morpholinomethyl-substituted silicone in which more than 98.7 mol % of the structural units are dimethylsiloxy units, i.e. in which structural unit (I) makes up at least nine hundred eighty-seven thousandths of all structural units of the silicone used.

In other words, silicones in which $m>77(n+o)$ resp. $(a+b+c)>77(n+o)$, are preferred.

Even further preferred post-treatment agents used according to the present invention contain a 4-morpholinomethyl-substituted silicone in which more than 99.5 mol % of the structural units are dimethylsiloxy units, i.e. in which structural unit (I) makes up at least nine hundred ninety-five thousandths of all structural units of the silicone used.

In other words, silicones in which $m>200(n+o)$ resp. $(a+b+c)>200(n+o)$, are preferred.

In summary, preferred post-treatment agents used according to the present invention are characterized in that they contain at least one 4-morpholinomethyl-substituted silicone in which
$m>(n+o)$ resp. $(a+b+c)>(n+o)$, preferably
$m>8(n+o)$ resp. $(a+b+c)>8(n+o)$, particularly preferably
$m>25(n+o)$ resp. $(a+b+c)>25(n+o)$, more preferably
$m>77(n+o)$ resp. $(a+b+c)>77(n+o)$, and in particular
$m>200(n+o)$ resp. $(a+b+c)>200(n+o)$.

A further method preferred according to the present invention is characterized in that the post-treatment agent used in step a) contains hydroxy-terminated 4-morpholinomethyl-substituted silicone(s) in which the molar ratio of hydroxy to alkoxy is in the range from about 0.2:1 to about 0.4:1, preferably in the range from 1:0.8 to 1:1.1.

A further method preferred according to the present invention is characterized in that the weight-average molar mass of the 4-morpholinomethyl-substituted silicone of formula (V) used in step a) is in the range from about 2000 to about 1,000,000 g=mol$^{-1}$, preferably in the range from about 5000 to about 200,000 gmol$^{-1}$.

The average molar masses of amino-substituted silicones are measurable, for example, by gel permeation chromatography (GPC) at room temperature in polystyrene. Styragel μ columns can be selected as columns, THF as an eluent, and 1 ml/min as a flow rate. Detection is accomplished preferably by refractometry using a UV meter.

4-Morpholinomethyl-substituted silicones of formula (V) that are particularly preferred according to the present invention are contained in the raw material Belsil ADM 8301 E (ex Wacker Silicones) under the name Amodimethicone/Morpholinomethyl Silsesquioxane. Belsil ADM 8301 E represents a microemulsion and is made up of the following constituents: Amodimethicone/Morpholinomethyl Silsesquioxane (about 10 wt %); Trideceth-5 (about 5 wt %); glycerol (about 2.5 wt %); phenoxyethanol (about 0.45 wt %); and water (about 82.05 wt %).

It has become apparent that the method according to the present invention can be further improved if specific nonionic components are likewise contained in the post-treatment agents used according to the present invention. These nonionic components moreover have positive effects on the shelf stability of the post-treatment agents used according to the present invention. Nonionic components that are particularly suitable here are ethoxylates of decanol, undecanol, dodecanol, tridecanol, myristyl alcohol, cetyl alcohol, and/or stearyl alcohol. Ethoxylated tridecanols have proven to be particularly suitable, and are incorporated with particular preference into the post-treatment agents used according to the present invention. Branched ethoxylated tridecanols are particularly preferred, in particular branched tridecanols having 3 to 5 ethylene oxide units in the molecule. Post-treatment agents used particularly preferably according to the present invention contain, based in each case on their weight, about 0.001 to about 5 wt %, preferably about 0.005 to about 3.5 wt %, particularly preferably about 0.01 to about 2 wt %, more preferably about 0.05 to about 1 wt %, and in particular about 0.1 to about 0.5 wt % branched ethoxylated tridecanol, particularly preferably about 0.001 to about 5 wt %, preferably about 0.005 to about 3.5 wt %, particularly preferably about 0.01 to about 2 wt %, more preferably about 0.05 to about 1 wt %, and in particular about 0.1 to about 0.5 wt % branched ethoxylated tridecanol having 3 to 5 ethylene oxide units in the molecule.

Further surfactants and emulsifier agents are preferably not contained, or are contained only in small quantities, in the post-treatment agents used according to the present invention. Post-treatment agents preferably used according to the present invention contain, based on the total weight of the agent, about 0.001 to a maximum of about 6 wt % surfactant(s), the aforementioned ethoxylates of decanol, undecanol, dodecanol, tridecanol, myristyl alcohol, cetyl alcohol, and/or stearyl alcohol being included.

The post-treatment agents used according to the present invention are preferably of low viscosity, i.e. are formulated with a viscosity (measured at about 20° C.) in the range from about 10 to about 2000 mPas, preferably about 20 to about 1000 mPas, particularly preferably about 50 to about 800 mPas. It has moreover been found that thickening polymers can attenuate the effect according to the present invention, so that preferred post-treatment agents used according to the present invention are characterized in that they contain thickening polymers in a total quantity of ≤2.5 wt %, preferably ≤1 wt %, more preferably ≤0.5 wt %, and in particular ≤0.01 wt %, based in each case on the weight of the post-treatment agent.

The post-treatment agents used according to the present invention can contain further ingredients. It is preferred in this context to use polyvalent alcohols that have moisture-donating properties. Post-treatment agents used according to the present invention that contain at least one polyvalent alcohol, preferably selected from the group of sorbitol and/or glycerol and/or 1,2-propylene glycol or mixtures thereof, in a total quantity from about 0.05 to about 15 wt %, preferably about 0.1 to about 10 wt %, particularly preferably about 0.15 to about 5 wt %, and in particular about 0.15 to about 1 wt %, based in each case on the weight of the post-treatment agent, are preferred here. For specific utilization sectors it can be advantageous to use only one of the three aforementioned preferred polyvalent alcohols. In most cases, glycerol is preferred. Mixtures of two of the three polyvalent alcohols, or of all three polyvalent alcohols, can nevertheless be preferred in other utilization sectors. A mixture of glycerol, sorbitol, and 1,2-propylene glycol at a weight ratio of about 1:(0.5-1):(0.1-0.5) has proven particularly advantageous here.

Besides sorbitol, glycerol, and 1,2-propylene glycol, further polyvalent alcohols that are suitable are those having at least 2OH groups, preferably mannitol, xylitol, polyethylene glycol, polypropylene glycol, and mixtures thereof. Among these compounds those having 2 to 12OH groups, and in particular those having 2, 3, 4, 5, 6, or 10OH groups, are preferred.

Polyhydroxy compounds having 2OH groups are, for example, glycol ($CH_2(OH)CH_2OH$) and other 1,2-diols such as H—$(CH_2)_n$—$CH(OH)CH_2OH$ where n=2, 3, 4, 5, 6, 7, 8, 9, 10, 11, 12, 13, 14, 15, 16, 17, 18, 19, 20. 1,3-Diols such as H—$(CH_2)_n$—$CH(OH)CH_2CH_2OH$, where n=1, 2, 3, 4, 5, 6, 7, 8, 9, 10, 11, 12, 13, 14, 15, 16, 17, 18, 19, 20, are also usable according to the present invention. The (n,n+1)-resp. (n,n+2)-diols having non-terminal OH groups can likewise be used. Important representatives of polyhydroxy compounds having 2OH groups are also the polyethylene and polypropylene glycols. Further preferred polyvalent alcohols that can be used are, for example, xylitol, propylene glycols, polyethylene glycols, in particular those having average molecular weights from about 200 to about 800. It is particularly preferred to use glycerol, so that agents that contain no other polyvalent alcohols besides glycerol are particularly preferred.

The use of specific care-providing substances in the post-treatment agents of the method according to the present invention is preferred in terms of post-treatment after an oxidative hair treatment.

Post-treatment agents preferably used according to the present invention are characterized in that they additionally contain care-providing substance(s) in a total quantity from about 0.001 to about 10 wt %, preferably about 0.005 to about 7.5 wt %, particularly preferably about 0.01 to about 5 wt %, and in particular about 0.05 to about 2.5 wt %, based in each case on the total weight of the post-treatment agent. Preferred care-providing substance(s) are selected from at least one of the groups recited below:

i. L-carnitine and/or salts thereof;
ii. taurine and/or salts thereof;
iii. niacinamide;
iv. ubiquinone;
v. ectoin;
vi. vitamins;
vii. flavonoids.

Post-treatment agents used according to the present invention can particularly preferably contain one or more amino acids as a further ingredient. Amino acids usable particularly preferably according to the present invention derive from the group of glycine, alanine, valine, leucine, isoleucine, phenylalanine, tyrosine, tryptophan, proline, aspartic acid, glutamic acid, asparagine, glutamine, serine, threonine, cysteine, methionine, lysine, arginine, histidine, β-alanine, 4-aminobutyric acid (GABA), betaine, L-cystine (L-Cyss), L-carnitine, L-citrulline, L-theanine, 3',4'-dihydroxy-L-phenylalanine (L-DOPA), 5'-hydroxy-L-tryptophan, L-homocysteine, S-methyl-L-methionine, cysteine sulfoxide (L-alliine), L-trans-4-hydroxyproline, L-5-oxoproline (L-pyroglutamic acid), L-phosphoserine, creatine, 3-methyl-L-histidine, L-ornithine; both the individual amino acids and mixtures can be used.

Preferred post-treatment agents used according to the present invention contain one or more amino acids in narrower quantity ranges. Post-treatment agents used according to the present invention are characterized here in that they contain as a care-providing substance about 0.01 to about 5 wt %, preferably about 0.02 to about 2.5 wt %, particularly preferably about 0.05 to about 1.5 wt %, more preferably about 0.075 to about 1 wt %, and in particular about 0.1 to about 0.25 wt % amino acid(s), preferably from the group of glycine and/or alanine and/or valine and/or lysine and/or leucine and/or threonine, based in each case on the total weight of the post-treatment agent.

The post-treatment agent used according to the present invention can be formulated as a low-viscosity water-based emulsion, a spray, a cream, gel, lotion, paste, shampoo, or conditioner.

The method according to the present invention encompasses an oxidative hair treatment and an application, within a time period from one second to 24 hours subsequent thereto, of a post-treatment agent onto keratinic fibers.

A great advantage of the post-treatment agents used in step b) is that they are effective not only when utilized immediately after the oxidative hair treatment, but instead can be utilized up to 24 hours thereafter with no risk of attenuation of the effect due to external influences. It is thereby possible, for example, to carry out step a) of the method according to the present invention in the afternoon, and to perform the oxidative hair treatment only the next morning after shampooing.

Methods preferred according to the present invention are characterized in that the time period between method steps a) and b) is from about 2 seconds to about 20 minutes, preferably about 30 seconds to about 10 minutes, particularly preferably about 1 to about 5 minutes.

Further methods preferred according to the present invention are characterized in that the post-treatment agent applied in method step b) is allowed to act on the hair for a time period from about 2 seconds to about 120 minutes, preferably about 5 seconds to about 10 minutes, before it is rinsed out or before the hair is dried without rinsing.

Further methods preferred according to the present invention are characterized in that the post-treatment agent applied in method step b) is allowed to act on the hair for a time period from about 2 seconds to about 120 minutes, preferably about 5 seconds to about 10 minutes, before at least one of the following method steps b)i occurs:
rinsing out the hair;
drying the hair with a towel;
allowing the hair to air-dry;
blow-drying the hair;
drying the hair with a drying hood;
combinations of the aforementioned method steps.

The drying operation occurs preferably at a temperature from about 20° C. to about 150° C.

Particularly preferably, the drying operation resp. operations are not preceded by rinsing out of the hair. A method preferred according to the present invention is therefore characterized in that no rinsing out of the hair occurs after the application of the post-treatment agent performed in method step b) and the drying operation resp. operations. It can, however, also be preferred according to the present invention first to rinse out the hair after step a) and then to dry it before the treatment step b) occurs.

A method preferred according to the present invention is further characterized in that step a) encompasses the application of a coloring agent and/or lightening agent onto the keratinic fibers, which agent is obtained by mixing a composition (A) that contains at least one alkalizing agent with a composition (B) that contains at least one oxidizing agent in a cosmetic carrier, where composition (B) additionally contains at least one acylpyridinium derivative of formula (Acylpyr-I),

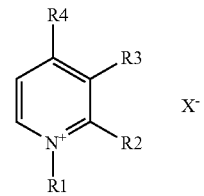

(Acylpyr-I), in which
R1 denotes a $C_1$ to $C_6$ alkyl group, a $C_2$ to $C_6$ alkenyl group, a $C_2$ to $C_6$ hydroxyalkyl group, a $C_1$ to $C_6$ alkoxy-$C_2$ to $C_6$ alkyl group, a carboxy $C_2$ to $C_6$ alkyl group, an aryl $C_1$ to $C_6$ alkyl group, a heteroaryl $C_1$ to $C_6$ alkyl group, an awl group, or a heteroaryl group,
R2, R3, and R4 mutually independently in each case denote hydrogen, a $C_1$ to $C_6$ alkyl group, a halogen atom, or a $C_1$ to $C_6$ acyl group, with the provision that at least one of the residues R2, R3, and R4 denotes a $C_1$ to $C_6$ acyl group, and
X$^-$ denotes a physiologically acceptable anion.

The composition (B) used in the methods and kits of parts according to the present invention and preferred according to the present invention contains as a first obligatory ingredient at least one acylpyridinium derivative of formula (Acylpyr-I) as explained above. It has been found, surprisingly, that an acylpyridinium derivative of this kind appears to interact synergistically with the post-treatment used according to the present invention, and resulted in an unexpected further reduction in hair damage.

Examples of the aforesaid substituents of the compounds of formula (Acylpyr-I) are recited below, but not in limiting fashion: Examples of $C_1$ to $C_6$ alkyl residues are the groups —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)$ $CH_2CH_3$, —$C(CH_3)_3$. Examples of a $C_2$ to $C_6$ alkenyl group are a prop-2-enyl group (allyl group), a 2-methyl-prop-2-enyl group, a but-3-enyl group, a but-2-enyl group, a pent-4-enyl group, or a pent-3-enyl group, the prop-2-enyl group being preferred. Examples of a $C_2$ to $C_6$ hydroxyalkyl group are —$CH_2CH_2OH$, —$CH_2CH_2CH_2OH$, —$CH_2CH(OH)CH_3$, and —$CH_2CH_2CH_2CH_2OH$, the —$CH_2CH_2OH$ group being preferred. Examples of $C_1$ to $C_6$ alkoxy-$C_2$ to $C_6$ alkyl groups are the groups —$CH_2CH_2OCH_3$, —$CH_2CH_2CH_2OCH_3$, —$CH_2CH_2OCH_2CH_3$, —$CH_2CH_2CH_2OCH_2CH_3$, —$CH_2CH_2OCH(CH_3)_2$, —$CH_2CH_2CH_2OCH(CH_3)_2$. Examples of a carboxy-$C_1$ to $C_6$ alkyl group are the carboxymethyl group, the 2-carboxyethyl group, or the 3-carboxypropyl group. Examples of aryl-$C_1$ to $C_6$ alkyl groups are the benzyl group and the 2-phenylethyl group. Examples of a heteroaryl-$C_1$ to $C_6$ alkyl group are the pyridin-2-ylmethyl group, the pyridin-3-ylmethyl group, the pyridin-4-ylmethyl group, the pyrimidin-2-ylmethyl group, the pyrrol-1-ylmethyl group, the pyrrol-1-ylethyl group, the pyrazol-1-ylmethyl group, or the pyrazol-1-ylethyl group. Examples of an aryl group are the phenyl group, the 1-naphthyl group, or the 2-naphthyl group. Examples of a heteroaryl group are the pyridin-2-yl group, the pyridin-3-yl group, the pyridin-4-yl group, the pyrimidin-2-yl group, the pyrrol-1-yl group, the pyrrol-2-yl group, the pyrazol-1-yl group, the pyrazol-3-yl group, or the pyrazol-4-yl group. Examples of a $C_1$ to $C_6$ acyl group are acetyl (1-oxoethyl), 1-oxopropyl, 1-oxobutyl, 1-oxopentyl, 1-oxo-2,2-dimethylpropyl, and 1-oxohexyl.

In an embodiment of the present invention, those compounds according to formula (Acylpyr-I) in which the residue R1 of the general structure (Acylpyr-I) denotes a $C_1$ to $C_6$ alkyl group, a $C_2$ to $C_6$ alkenyl group, or a $C_2$ to $C_6$ hydroxyalkyl group, are preferred. It is preferred according to the present invention if the residue R1 denotes a $C_1$ to $C_6$ alkyl group, preferably methyl, ethyl, n-propyl, or isopropyl, and particularly preferably methyl.

It has been found that the acetylpyridinium derivatives according to formula (I) possess particularly advantageous properties according to the present invention if they carry the acyl group in either the 2- or the 4-position on the pyridine ring. Preferred compounds of formula (Acylpyr-I) are furthermore those compounds in which either residue R2 or residue R4 denotes a $C_1$ to $C_6$ acyl group, preferably an acetyl group. It is furthermore preferred if one of the residues R2 or R4 denotes an acetyl group, while the other of these residues, and residue R3, each denote hydrogen. A further embodiment of the present invention is characterized in that the agent contains, as an acetylpyridinium derivative according to formula (I), at least one 2-acetylpyridinium derivative and/or 4-acetylpyridinium derivative.

Suitable acetylpyridinium derivatives are, in this context, the physiologically acceptable salts that contain, as a cation, an acetylpyridinium derivative selected from 4-acetyl-1-methylpyridinium, 4-acetyl-1-allylpyridinium, 4-acetyl-1-(2-hydroxyethyl)pyridinium, 2-acetyl-1-methylpyridinium, 2-acetyl-1-allylpyridinium, and 2-acetyl-1-(2-hydroxyethyl)pyridinium.

It is preferred if the anion $X^-$ according to formula (Acylpyr-I) is selected from halide, in particular chloride, bromide, and iodide, benzenesulfonate, p-toluenesulfonate, $C_1$ to $C_4$ alkylsulfonate, trifluoromethanesulfonate, acetate, trifluoroacetate, perchlorate, hemisulfate, hydrogen sulfate, tetrafluoroborate, hexachlorophosphate, or tetrachlorozincate. It is particularly preferred according to the present invention if the anion $X^-$ denotes hydrogen sulfate, p-toluenesulfonate, benzenesulfonate, or acetate. Extraordinarily preferably, the anion $X^-$ is p-toluenesulfonate.

Methods and kits particularly preferred according to the present invention are those characterized in that the acylpyridinium derivative according to formula (Acylpyr-I) is selected from the group constituted from 4-acetyl-1-methylpyridinium-p-toluene sulfonate, 4-acetyl-1-methylpyridinium benzenesulfonate, 4-acetyl-1-methylpyridinium hydrogen sulfate, 4-acetyl-1-methylpyridinium acetate, 4-acetyl-1-allylpyridinium-p-toluenesulfonate, 4-acetyl-1-allylpyridinium benzenesulfonate, 4-acetyl-1-allylpyridinium hydrogen sulfate, 4-acetyl-1-allylpyridinium acetate, 2-acetyl-1-methylpyridinium-p-toluenesulfonate, 2-acetyl-1-methylpyridinium benzenesulfonate, 2-acetyl-1-methylpyridinium hydrogen sulfate, 2-acetyl-1-methylpyridinium acetate, 2-acetyl-1-allylpyridinium-p-toluenesulfonate, 2-acetyl-1-allylpyridinium benzenesulfonate, 2-acetyl-1-allylpyridinium hydrogen sulfate, and 2-acetyl-1-allylpyridinium acetate.

Methods and kits preferred according to the present invention are characterized in that they contain as an acylpyridinium derivative according to formula (Acylpyr-I) a compound selected from 4-acetyl-1-methylpyridinium-p-toluenesulfonate and/or 2-acetyl-1-methylpyridinium-p-toluenesulfonate, in particular 4-acetyl-1-methylpyridinium-p-toluenesulfonate.

Those methods and kits which are characterized in that they one or more acylpyridinium derivative(s) of formula (Acylpyr-I), in a total quantity from about 0.001 to about 15 wt %, preferably from about 0.01 to about 10 wt %, and particularly preferably from about 0.1 to about 5 wt %, based in each case on the total weight of the coloring and/or lightening agent applied in method step b), have proven to be preferred according to the present invention.

Composition (B) used in the method according to the present invention contains as a second obligatory ingredient at least one oxidizing agent. Preferred oxidizing agents are selected from peroxo compounds, preferably selected from hydrogen peroxide, a solid addition compound of hydrogen peroxide with inorganic or organic compounds, such as sodium perborate, sodium percarbonate, magnesium percarbonate, sodium percarbamide, polyvinylpyrrolidone.n $H_2O_2$ (n is a positive number greater than 0), urea peroxide, and melamine peroxide, furthermore selected from diammonium peroxodisulfate (also referred to as ammonium persulfate), disodium peroxodisulfate (also referred to as sodium persulfate), and dipotassium peroxodisulfate (also referred to as potassium persulfate), and from mixtures of these oxidizing agents. Oxidizing agents used with very particular preference according to the present invention are aqueous hydrogen peroxide solutions. The concentration of a hydrogen peroxide solution is determined on the one hand by regulatory provisions and on the other hand by the desired effect; 6- to 12-weight-percent solutions in water are preferably used. Methods preferred according to the present invention are characterized in that the composition (B) that is used contains, based on its weight, about 1 to about 24 wt %, preferably about 4 to about 10 wt %, particularly preferably about 3 to about 6 wt % hydrogen peroxide (calculated as 100% $H_2O_2$).

The cosmetically acceptable carrier of composition (B) is preferably aqueous, alcoholic, or aqueous alcoholic. "Aqueous alcoholic" carriers are to be understood for purposes of the present invention as aqueous compositions containing about 3 to about 70 wt % of a $C_1$ to $C_4$ alcohol based on the total weight of composition (B), in particular ethanol resp. isopropanol. Compositions (B) preferred according to the present invention can additionally contain further organic solvents such as, for example, 4-methoxybutanol, ethyl diglycol, 1,2-propylene glycol, n-propanol, n-butanol, n-butylene glycol, glycerol, diethylene glycol monoethyl ether, and diethylene glycol mono-n-butyl ether. All water-soluble organic solvents are preferred in this context. An "aqueous" carrier contains, for purposes of the invention, water in a total quantity from about 35 to about 97 wt %, particularly preferably about 50 to about 90 wt %, particularly preferably about 60 to about 80 wt %, based in each case on the total weight of composition (B).

By preference according to the present invention, composition (B) has a weakly acid pH, preferably a pH value from pH about 2 to pH about 6, particularly preferably from pH about 2.5 to pH about 4.5, extraordinarily preferably from pH about 3.0 to pH about 4.0. The pH values for purposes of the present invention are pH values that were measured at a temperature of 22° C. One skilled in the art is familiar, for purposes of adjusting the pH, with common acidifying and alkalizing agents. Acidifying agents preferred according to the present invention are edible acids such as, for example, citric acid, acetic acid, malic acid, or tartaric acid, as well as dilute mineral acids.

The coloring and/or lightening agent applied in method step b) should be notable for very good miscibility of the two compositions (A) and (B). The coloring and/or lightening agent resulting from mixing is intended to have sufficient viscosity that the agent on the one hand can be applied easily, but on the other hand remains at the location of action during utilization and does not flow off the fibers.

To achieve sufficient thickening, the use of polymeric thickeners whose thickening properties change with pH is preferred. This property can be utilized particularly advantageously if the polymeric thickener is contained in the acidic oxidizing agent composition (B), since this agent experiences a large change in pH upon mixing to yield the coloring and/or lightening agent. Composition (B) therefore preferably contains at least one anionic polymeric thickener that results in an appreciable increase in viscosity at an alkaline pH. Preferably crosslinked, but also uncrosslinked, homo- or copolymers of acrylic acid or methacrylic acid are particularly preferred as such anionic polymeric thickening agents.

It has furthermore proven to be advantageous if composition (B) contains at least one stabilizer or complexing agent. Particularly preferred stabilizers are phenacetin, alkali benzoates (sodium benzoate), and salicylic acid.

The use of so-called complexing agents in composition (B) is also preferred according to the present invention. Complexing agents are substances that can complex metal ions. Preferred complexing agents are so-called chelate complexing agents, i.e. substances that form cyclic compounds with metal ions, where an individual ligand occupies more than one coordination site on a central atom, i.e. is at least "double-toothed." Usual chelate complexing agents that are preferred in the context of the present invention are, for example, polyoxycarboxylic acids, polyamines, ethylenediaminetetraacetic acid (EDTA), nitrilotriacetic acid (NTA), and hydroxyethanediphosphonic acids resp. alkali salts thereof. Also usable according to the present invention are complexing polymers, i.e. polymers that carry either in the main chain itself, or laterally thereto, functional groups that can act as ligands and react with suitable metal atoms, usually accompanied by the formation of chelate complexes. The polymer-bound ligands of the resulting metal complexes can derive from only one macromolecule or else can belong to different polymer chains. Complexing agents preferred according to the present invention are nitrogen-containing polycarboxylic acids, in particular EDTA, and phosphonates, by preference hydroxyalkane-resp. aminoalkanephosphonates, and in particular 1-hydroxyethane-1,1-diphosphonate (HEDP) resp. the di- or tetrasodium salt thereof, and/or ethylenediaminetetramethylenephosphonate (EDTMP) resp. the hexasodium salt thereof, and/or diethylenetriaminepentamethylenephosphonate (DTPMP) resp. the hepta- or octasodium salt thereof. Dipicolinic acid is likewise preferred.

Composition (A) used in the method according to the present invention and in the kit of parts contains as an obligatory ingredient at least one alkalizing agent. Oxidative coloring processes on keratin fibers usually proceed in an alkaline environment. In order to minimize stress on the keratin fibers and also on the skin, however, it is not desirable to establish too high a pH. It is therefore preferred if the pH of the coloring agent and/or lightening agent used in step b) is between about 7 and 11, in particular in the range from about S to about 10.5. The pH values for purposes of the present invention are pH values that have been measured at a temperature of 22° C.

The alkalizing agents usable according to the present invention in order to establish the preferred pH can be selected from the group of ammonia, basic amino acids, alkali hydroxides, alkanolamines, alkali metal metasilicates, alkali phosphates, and alkali hydrogen phosphates. Lithium, sodium, potassium preferably serve as alkali metal ions, in particular sodium or potassium.

The basic amino acids usable as alkalizing agents are preferably selected from the group of L-arginine, D-arginine, D,L-arginine, L-lysine, D-lysine, D,L-lysine, particularly preferably L-arginine, D-arginine, D,L-arginine used as an alkalizing agent for purposes of the invention.

The alkali hydroxides usable as alkalizing agents are preferably selected from the group of sodium hydroxide and potassium hydroxide.

The alkanolamines usable as alkalizing agents are preferably selected from primary amines having a $C_2$ to $C_6$ alkyl basic structure that carries at least one hydroxyl group. Particularly preferred alkanolamines are selected from the group that is constituted from 2-aminoethan-1-ol (monoethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropane-1,2-diol, 2-amino-2-methylpropane-1,3-diol. Alkanolamines very particularly preferred according to the present invention are selected from the group of: 2-aminoethan-1-ol, 2-amino-2-methylpropan-1-ol, and 2-amino-2-methylpropane-1,3-diol.

For oxidative coloring methods, it is usual that, shortly before application onto the fibers, in particular the hair, a coloring composition (A), which contains at least one alkalizing agent as well as one or more oxidation dye precursors and optionally one or more substantive dyes, is mixed with an aqueous oxidizing-agent-containing composition (B) to yield a ready-to-use coloring agent and is then applied onto the fibers, in particular the hair.

For oxidative lightening methods, it is usual that, shortly before application onto the fibers, in particular the hair, a lightening composition (A), which contains at least one alkalizing agent as well as optionally one or more substantive dyes, is mixed with an aqueous oxidizing-agent-containing composition (B) to yield a ready-to-use coloring agent and is then applied onto the fibers, in particular the hair.

The coloring and/or lightening composition (A) and the oxidizing-agent-containing composition (B) are usually coordinated with one another in such a way that with a mixing ratio of about 1:1 (based on parts by weight) an initial concentration of hydrogen peroxide from about 0.5 to about 12 wt %, preferably about 2 to about 10 wt %, particularly preferably about 3 to about 6 wt % hydrogen peroxide (calculated as 100% $H_2O_2$) is present in the hair coloring agent, based on the weight of the coloring and/or lightening agent. It is, however, equally possible to coordinate the coloring and/or lightening composition (A) and the oxidizing-agent-containing composition (B) with one another in such a way that the concentrations necessary in the ready-to-use coloring and/or lightening agent are obtained by means of mixing ratios other than about 1:1, for example by a weight-related mixing ratio of about 1:2 or about 1:3 or even about 2:3. Methods preferred according to the present invention are characterized in that the ready-to-use coloring and/or lightening agent used in method step b) contains an initial quantity of hydrogen peroxide from about 0.5 to about 12 wt %, preferably about 2 to about 10 wt %, particularly preferably about 3 to about 6 wt % hydrogen peroxide (calculated as 100% $H_2O_2$), based in each case on the weight of the coloring and/or lightening agent.

Methods and kits of parts preferred according to the present invention are characterized in that the ready-to-use coloring and/or lightening agent used in method step b) contains at least one cosmetic oil in a total quantity from about 5 to about 50 wt %, preferably about 8 to about 40 wt %, particularly preferably about 12 to about 30 wt %, extraordinarily preferably about 15 to about 25 wt %, based in each case on the weight of the coloring and/or lightening agent.

The use of hydrogen peroxide or addition products thereof with organic resp. inorganic compounds is often insufficient for a coloring operation that requires considerable lightening of very dark hair. A combination of hydrogen peroxide and peroxodisulfate salts (persulfate salts) is generally used in such cases. Preferred persulfate salts are ammonium peroxydisulfate, potassium peroxydisulfate, sodium peroxydisulfate, and mixtures thereof.

The at least one persulfate salt is contained preferably in a total quantity from about 0.1 to about 25 wt %, particularly preferably in a total quantity from about 1 to about 15 wt %, based on the weight of the ready-to-use coloring agent.

Further methods and kits of parts preferred according to the present invention are characterized in that the composition (B) contains at least one cosmetic oil in a total quantity from about 10 to about 80 wt %, based on the weight of composition (B). The cosmetic oil is liquid under standard conditions (20° C., 1013.25 mbar); essential oils and perfume oils resp. fragrances are not included among the cosmetic oils. The cosmetic oils that are liquid under standard conditions are not miscible with water. "Essential oils" are understood according to the present invention as mixtures of volatile components that are produced by steam distillation from vegetable raw materials, e.g. citrus oils. When a "cosmetic oil" is discussed in the present Application, this always refers to a cosmetic oil that is not a fragrance and not an essential oil, is liquid under standard conditions, and is not miscible with water.

The definition of a "fragrance" for purposes of the present Application corresponds to the definition usual in the art, as may be gathered from the RÖMPP Chemie Lexikon [Chemical Lexicon] as of December 2007. According to the latter, a fragrance is a chemical compound having an odor and/or taste that excites the receptors of the hair cells of the olfactory system (adequate stimulus). The physical and chemical properties necessary for this are a low molar mass of at most 300 g/mol, a high vapor pressure, minimal water solubility and high lipid solubility, as well as weak polarity and the presence of at least one osmophoric group in the molecule. In order to distinguish volatile low-molecular-weight substances that are usually (and also for purposes of the present Application) viewed and utilized not as fragrances but instead principally as solvents, for example ethanol, propanol, isopropanol, and acetone, from fragrances according to the present invention, fragrances according to the present invention have a molar mass from about 74 to about 300 g/mol, contain at least one osmophoric group in the molecule, and have an odor and/or taste, i.e. they excite the receptors of the hair cells of the olfactory system.

Cosmetic oils preferred according to the present invention are selected from natural and synthetic hydrocarbons, particularly preferably from paraffin oils, $C_{18}$ to $C_{30}$ isoparaffins, in particular isoeicosane, polyisobutenes, and polydecenes, which are obtainable, for example, under the name Emery 3004, 3006, 3010 or under the name Ethylflo® from Albemarle or Nexbase® 2004G from Nestle, further selected from $C_8$ to $C_{16}$ isoparaffins, in particular from isodecane, isododecane, isotetradecane, and isohexadecane as well as mixtures thereof, as well as 1,3-di-(2-ethylhexyl)cyclohexane (obtainable e.g. under the trade name Cetiol® S from BASF).

Further cosmetic oils preferred according to the present invention are selected from benzoic acid esters of linear or branched $C_{8-22}$ alkanols. Benzoic acid $C_{12}$ to $C_{15}$ alkyl esters, obtainable e.g. as the commercial product Finsolv® TN, benzoic acid isostearyl esters, obtainable e.g. as the commercial product Finsolv® SB, ethylhexyl benzoate, obtainable e.g. as the commercial product Finsolv® EB, and benzoic acid octyldodecyl esters, obtainable e.g. as the commercial product Finsolv® BOD, are particularly preferred.

Further cosmetic oils preferred according to the present invention are selected from fatty alcohols having 6 to 30 carbon atoms, which are unsaturated or branched and saturated or branched and unsaturated. The branched alcohols are often also referred to as "Guerbet alcohols," since they are obtainable via the Guerbet reaction. Preferred alcohol oils are 2-hexyldecanol (Eutanol® G 16), 2-octyldodecanol (Eutanol® G), 2-ethyhexyl alcohol, and isostearyl alcohol.

Further preferred cosmetic oils are selected from mixtures of Guerbet alcohols and Guerbet alcohol esters, e.g. the commercial product Cetiol® PGL (2-hexyldecanol and 2-hexyldecyl laurate).

Further cosmetic oils preferred according to the present invention are selected from triglycerides (=triesters of glycerol) of linear or branched, saturated or unsaturated, optionally hydroxylated $C_{8-30}$ fatty acids. The use of natural oils, e.g. amaranth seed oil, apricot kernel oil, argan oil, avocado oil, babassu oil, cottonseed oil, borage seed oil, camelina oil, thistle oil, peanut oil, pomegranate seed oil, grapefruit seed oil, hemp oil, hazelnut oil, elderberry seed oil, blackcurrant seed oil, jojoba oil, linseed oil, macadamia nut oil, corn oil, almond oil, manila oil, evening primrose oil, olive oil, palm oil, palm kernel oil, para nut oil, pecan nut oil, peach kernel oil, rapeseed oil, castor oil, sea buckthorn pulp oil, sea buckthorn seed oil, sesame oil, soy oil, sunflower oil, grapeseed oil, walnut oil, wild rose oil, wheat genu oil, and the liquid components of coconut oil and the like, can be particularly preferred. Synthetic triglyceride oils are also preferred, however, in particular Capric/Caprylic Triglycerides, e.g. the commercial products Myritol® 318, Myritol® 331 (BASF), or Miglyol® 812 (Hills) having unbranched fatty acid esters, as well as glyceryl triisostearine having branched fatty acid esters.

Further cosmetic oils particularly preferred according to the present invention are selected from dicarboxylic acid esters of linear or branched $C_2$ to $C_{10}$ alkanols, in particular diisopropyl adipate, di-n-butyl adipate, di-(2-ethylhexyl) adipate, dioctyl adipate, diethyl-/di-n-butyl/dioctyl sebacate, diisopropyl sebacate, dioctyl malate, dioctyl maleate, dicaprylyl maleate, diisooctyl succinate, di-2-ethylhexyl succinate, and di-(2-hexyldecyl) succinate.

Further cosmetic oils particularly preferred according to the present invention are selected from esters of linear or branched, saturated or unsaturated fatty alcohols having 2 to 30 carbon atoms with linear or branched, saturated or unsaturated fatty acids having 2 to 30 carbon atoms, which can be hydroxylated. These include 2-hexyldecyl stearate (Eutanol® G 16 S), 2-hexyldecyl laurate, isodecyl neopentanoate, isononyl isononanoate, 2-ethylhexyl palmitate (Cegesoft® C 24), and 2-ethylhexyl stearate (Cetiol® 868). Also preferred are isopropyl myristate, isopropyl palmitate, isopropyl stearate, isopropyl isostearate, isopropyl oleate, isooctyl stearate, isononyl stearate, isocetyl stearate, isononyl isononanoate, isotridecyl isononanoate, cetearyl isononanoate, 2-ethylhexyl laurate, 2-ethylhexyl isostearate, 2-ethylhexyl cocoate, 2-octyldodecyl palmitate, butyl octanoic acid 2-butyl octanoate, diisotridecyl acetate, n-butyl stearate, n-hexyl laurate, n-decyl oleate, oleyl oleate, oleyl erucate, erucyl oleate, erucyl erucate, ethylene glycol dioleate, and ethylene glycol dipalmitate.

Further cosmetic oils preferred according to the present invention are selected from addition products of 1 to 5 propylene oxide units with mono- or polyvalent $C_{8\text{-}22}$ alkanols such as octanol, decanol, decanediol, lauryl alcohol, myristyl alcohol, and stearyl alcohol, e.g. PPG-2 Myristyl Ether and PPG-3 Myristyl Ether (Witconol® APM).

Further cosmetic oils preferred according to the present invention are selected from addition products of at least 6 ethylene oxide and/or propylene oxide units with mono- or polyvalent $C_{3\text{-}22}$ alkanols such as glycerol, butanol, butanediol, myristyl alcohol, and stearyl alcohol, which can be esterified if desired, e.g. PPG-14 Butyl Ether (Ucon Fluid® AP), PPG-9 Butyl Ether (Breox® B25), PPG-10 Butanediol (Macol® 57), PPG-15 Stearyl Ether (Arlamol® E), and glycereth-7 diisonoanoate.

Further cosmetic oils preferred according to the present invention are selected from $C_8$ to $C_{22}$ fatty alcohol esters of monovalent or polyvalent $C_2$ to $C_7$ hydroxycarboxylic acids, in particular the esters of glycolic acid, lactic acid, malic acid, tartaric acid, citric acid, and salicylic acid. Such esters based on linear $C_{14/15}$ alkanols, e.g. $C_{12}$ to $C_{15}$ alkyl lactate, and on $C_{12/13}$ alkanols branched in the 2-position, can be obtained under the trade name Cosmacol® from Nordmann, Rassmann GmbH & Co., Hamburg, in particular the commercial products Cosmacol® ESI, Cosmacol® EMI, and Cosmacol® ETI.

Further cosmetic oils preferred according to the present invention are selected from symmetrical, asymmetrical, or cyclic esters of carbonic acid with $C_{3\text{-}22}$ alkanols, $C_{3\text{-}22}$ alkanediols, or $C_{3\text{-}22}$ alkanetriols, e.g. dicaprylyl carbonate (Cetiol® CC), or the esters according to the teaching of DE 19756454 A1, in particular glycerol carbonate.

Further cosmetic oils that can be preferred according to the present invention are selected from esters of dimers of unsaturated $C_{12}$ to $C_{22}$ fatty acids (dimer fatty acids) with monovalent linear, branched, or cyclic $C_2$ to $C_{18}$ alkanols or with polyvalent linear or branched $C_2$ to $C_6$ alkanols.

Further cosmetic oils that are suitable according to the present invention are selected from among the silicone oils that include, for example, dialkyl- and alkylarylsiloxanes such as e.g. cyclopentasiloxane, cyclohexasiloxane, dimethylpolysiloxane, and methyphenylpolysiloxane, but also hexamethyldisiloxane, octamethyltrisiloxane, and decamethyltetrasiloxane. Volatile silicone oils, which can be cyclic, can be preferred, for example octamethylcyclotetrasiloxane, decamethylcyclopentasiloxane, and dodecamethylcyclohexasiloxane, as well as mixtures thereof such as those contained, for example, in the commercial products DC 244, 245, 344, and 345 of Dow Corning. Also suitable are volatile linear silicone oils, in particular hexamethyldisiloxane ($L_2$), octamethyltrisiloxane ($L_3$), decamethyltetrasiloxane ($L_4$), as well as any mixtures of two or three of $L_2$, $L_3$, and/or $L_4$, preferably mixtures such as those contained e.g. in the commercial products DC 2-1184, Dow Corning® 200 (0.65 cSt), and Dow Corning® 200 (1.5 cSt) of Dow Corning. Preferred nonvolatile silicone oils are selected from higher-molecular-weight linear dimethylpolysiloxanes, obtainable commercially e.g. under the name Dow Corning 190, Dow Corning® 200 Fluid, having kinematic viscosities (25° C.) in the range from about 5 to about 100 cSt, preferably about 5 to about 50 cSt, or even about 5 to about 10 cSt, and dimethylpolysiloxane having a kinematic viscosity (25° C.) of approximately 350 cSt.

It can be extraordinarily preferred according to the present invention to use mixtures of the aforementioned cosmetic oils.

Preferred compositions (B) used according to the present invention are characterized in that the cosmetic oil is selected from natural and synthetic hydrocarbons, particularly preferably from paraffin oils, $C_{18}$ to $C_{30}$ isoparaffins, in particular isoeicosane, polyisobutenes, and polydecenes, $C_8$ to $C_{16}$ isoparaffins, and 1,3-di-(2-ethylhexyl)cyclohexane; benzoic acid esters of linear or branched $C_{8\text{-}22}$ alkanols; fatty alcohols having 6 to 30 carbon atoms, which are unsaturated or branched and saturated or branched and unsaturated; triglycerides of linear or branched, saturated or unsaturated, optionally hydroxylated $C_{8\text{-}30}$ fatty acids, in particular natural oils; dicarboxylic acid esters of linear or branched $C_2$ to $C_{10}$ alkanols; esters of linear or branched, saturated or unsaturated fatty alcohols having 2 to 30 carbon atoms with linear or branched, saturated or unsaturated fatty acids having 2 to 30 carbon atoms, which can be hydroxylated; addition products of 1 to 5 propylene oxide units with mono- or polyvalent $C_{8\text{-}22}$ alkanols; addition products of at least 6 ethylene oxide and/or propylene oxide units with mono- or polyvalent $C_{3\text{-}22}$ alkanols; $C_8$ to $C_{22}$ fatty alcohol esters of monovalent or polyvalent $C_2$ to $C_7$ hydroxycarboxylic acids; symmetrical, asymmetrical, or cyclic esters of carbonic acid with $C_{3\text{-}22}$ alkanols, $C_{3\text{-}22}$ alkanediols, or $C_{3\text{-}22}$ alkanetriols; esters of dimers of unsaturated $C_{12}$ to $C_{22}$ fatty acids (dimer fatty acids) with monovalent linear, branched, or cyclic $C_2$ to $C_{18}$ alkanols or with polyvalent linear or branched $C_2$ to $C_6$ alkanols; silicone oils; and mixtures of the aforementioned substances.

Preferred methods and kits of parts according to the present invention are characterized in that the composition (B) used according to the present invention contains at least one cosmetic oil in a total quantity from about 12 to about 70 wt %, preferably about 14 to about 60 wt %, particularly preferably about 15 to about 52 wt %, and extraordinarily preferably about 17 to about 35 wt %, based in each case on the weight of composition (B).

Further preferred methods and kits of parts according to the present invention are characterized in that the composition (B) used according to the present invention contains at least one surfactant.

When selecting surfactants suitable according to the present invention, it is particularly preferred to use a mixture of surfactants in order to allow optimum adjustment of the stability of the oxidizing agent compositions (B) used according to the present invention.

Preferred methods and kits of parts according to the present invention are characterized in that the surfactant contained in composition (B) is selected from nonionic surfactants and anionic surfactants and from mixtures thereof. Nonionic surfactants used with particular preference are selected from castor oil ethoxylated with about 20 to about 100 mol ethylene oxide per mol, ethoxylated $C_8$ to $C_{24}$ alkanols having about 10 to about 100 mol ethylene oxide per mol, ethoxylated $C_8$ to $C_{24}$ carboxylic acids having about 10 to about 100 mol ethylene oxide per mol, sorbitan monoesters, ethoxylated with about 20 to about 100 mol ethylene oxide per mol, of linear saturated and unsaturated $C_{12}$ to $C_{30}$ carboxylic acids, which can be hydroxylated, in particular those of myristic acid, palmitic acid, stearic acid, or mixtures of these fatty acids, alkylmono- and -oligoglycosides having 8 to 22 carbon atoms in the alkyl residue and ethoxylated analogs thereof, and mixtures of the aforesaid substances.

Castor oil ethoxylated with about 40 to about 80 mol ethylene oxide per mol is preferably contained in the compositions (B) preferably used according to the present invention.

The ethoxylated $C_8$ to $C_{24}$ alkanols have the formula $R^1O(CH_2CH_2O)_nH$, where $R^1$ denotes a linear or branched alkyl residue and/or alkenyl residue having 8 to 24 carbon atoms, and n (the average number of ethylene oxide units per molecule) denotes numbers from 10 to 100, preferably 10 to 30, particularly preferably about 15 to about 25 mol ethylene oxide per 1 mol caprylyl alcohol, 2-ethylhexyl alcohol, capryl alcohol, lauryl alcohol, isotridecyl alcohol, myristyl alcohol, cetyl alcohol, palmitoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol, and brassidyl alcohol, as well as industrial mixtures thereof. Adducts of 10 to 100 mol ethylene oxide with industrial fatty alcohols having 12 to 18 carbon atoms, for example coconut, palm, palm kernel, or tallow fatty alcohol, are also suitable. Laureth-10, Laureth-12, Laureth-15, Laureth-20, Laureth-30, Myreth-10, Myreth-12, Myreth-15, Myreth-20, Myreth-30, Ceteth-10, Ceteth-12, Ceteth-15, Ceteth-20, Ceteth-30, Steareth-10, Steareth-12, Steareth-15, Steareth-20, Steareth-30, Oleth-10, Oleth-12, Oleth-15, Oleth-20, Oleth-30, Ceteareth-10, Ceteareth-15, Ceteareth-12, Ceteareth-15, Ceteareth-20, Ceteareth-30, as well as Coceth-10, Coceth-12, Coceth-15, Coceth-20, and Coceth-30, are particularly preferred.

The ethoxylated $C_8$ to $C_{24}$ carboxylic acids have the formula $R^1O(CH_2CH_2)_nH$, where $R^1O$ denotes a linear or branched, saturated or unsaturated acyl residue having 8 to 24 carbon atoms and n (the average number of ethylene oxide units per molecule) denotes numbers from 10 to 100, preferably about 10 to about 30 mol ethylene oxide per 1 mol caprylic acid, 2-ethylhexanoic acid, capric acid, lauric acid, isotridecanoic acid, myristic acid, cetylic acid, palmitoleic acid, stearic acid, isostearic acid, oleic acid, elaidic acid, petroselic acid, arachidic acid, gadoleic acid, behenic acid, erucic acid, and brassidic acid, as well as industrial mixtures thereof. Adducts of about 10 to about 100 mol ethylene oxide with industrial fatty acids having 12 to 18 carbon atoms, for example coconut, palm, palm kernel, or tallow fatty acid, are also suitable. PEG-50 monostearate, PEG-100 monostearate, PEG-50 monooleate, PEG-100 monooleate, PEG-50 monolaurate, and PEG-100 monolaurate are particularly preferred.

Preferred sorbitan monoesters, ethoxylated with about 20 to about 100 mol ethylene oxide per mol, of linear saturated and unsaturated $C_{12}$ to $C_{30}$ carboxylic acids, which can be hydroxylated, are selected from Polysorbate-20, Polysorbate-40, Polysorbate-60, and Polysorbate-80.

$C_8$ to $C_{22}$ alkylmono- and -oligoglycosides are also preferably used. $C_8$ to $C_{22}$ alkylmono- and -oligoglycosides represent known, commercially usual surfactants and emulsifier agents. They are manufactured in particular by reacting glucose or oligosaccharides with primary alcohols having 8 to 22 carbon atoms. With regard to the glycoside residue, both monoglycosides in which a cyclic sugar residue is bound glycosidically to the fatty alcohol, and oligomeric glycosides having a degree of oligomerization up to approximately 8, preferably 1 to 2, are suitable. The degree of oligomerization is a statistical average that is based on a homolog distribution that is usual for industrial products of this kind. Products that are obtainable under the name Plantacare® contain a glucosidically bound $C_8$ to $C_{16}$ alkyl group on an oligoglucoside residue whose average degree of oligomerization is 1 to 2, in particular 1.2 to 1.4. Particularly preferred $C_8$ to $C_{22}$ alkyl mono- and -oligoglycosides are selected from octyl glucoside, decyl glucoside, lauryl glucoside, palmityl glucoside, isostearyl glucoside, stearyl glucoside, arachidyl glucoside, and behenyl glucoside, as well as mixtures thereof. The acyl glucamides derived from glucamine are also suitable as nonionic oil-in-water emulsifier agents.

Anionic surfactants suitable in the compositions (B) used according to the present invention are all anionic surface-active substances suitable for use on the human body, which comprise an anionic group imparting water solubility, for example a carboxylate, sulfate, sulfonate, or phosphate group, and a lipophilic alkyl group having approximately 8 to 30 carbon atoms, preferably 8 to 24 carbon atoms, in the molecule. Glycol ether or polyglycol ether groups, ester, ether, and amide groups, and hydroxyl groups can additionally be contained in the molecule. Examples of suitable anionic surfactants are, in each case in the form of the sodium, potassium, and ammonium salts and the mono-, di, and trialkanolammonium salts having 2 to 4 carbon atoms in the alkanol group: linear and branched fatty acids having 8 to 30 carbon atoms (soaps), polyethoxylated ethercarboxylic acids, acyl sarcosides, acyl taurides, acyl isethionates, sulfosuccinic acid mono- and dialkyl esters and sulfosuccinic acid monoalkylpolyoxyethyl esters having 1 to 6 ethylene oxide groups, linear alkanesulfonates, linear alpha-olefinsulfonates, sulfonates of unsaturated fatty acids having up to 6 double bonds, alpha-sulfo fatty acid methyl esters of fatty acids, $C_8$ to $C_{20}$ alkyl sulfates and $C_8$ to $C_{20}$ alkyl ether sulfates having up to 15 oxyethyl groups, mixtures of surface-active hydroxysulfonates, sulfated hydroxyalkyl polyethylene glycol ethers and/or hydroxyalkylene propylene glycol ethers, esters of tartaric acid or citric acid with ethoxylated or propoxylated fatty alcohols, optionally polyethoxylated alkyl and/or alkenyl ether phosphates, sulfated fatty acid alkylene glycol esters, as well as monoglyceride sulfates and monoglyceride ether sulfates.

Preferred anionic surfactants are soaps, $C_8$ to $C_{20}$ alkyl sulfates, $C_8$ to $C_{20}$ alkyl ether sulfates, and $C_8$ to $C_{20}$ ether carboxylic acids having 8 to 20 carbon atoms in the alkyl group and up to 12 ethylene oxide groups in the molecule. Sodium cetearyl sulfate is particularly preferred.

Preferably the total quantity of at least one surfactant in the oxidizing agent composition (B) is about 0.1 to about 5 wt %, preferably about 0.5 to about 3 wt %, and particularly preferably about 1 to about 2 wt %, based in each case on the total weight of the oxidizing agent composition (B).

Particularly preferably, the oxidizing agent composition (B) used according to the present invention contains a total of about 0.1 to about 5 wt %, preferably about 0.5 to about 3 wt %, and particularly preferably about 1 to about 2 wt %, of a mixture of nonionic and anionic surfactants, based in each case on the total weight of the oxidizing agent composition (B).

Further preferred methods according to the present invention are characterized in that the composition (B) used according to the present invention contains at least one linear saturated alkanol having 12 to 30 carbon atoms.

Preferred linear saturated alkanols having 12 to 30 carbon atoms, in particular having 16 to 22 carbon atoms, are selected from cetyl alcohol, stearyl alcohol, arachidyl alcohol, behenyl alcohol, and lanolin alcohol, as well as mixtures of these alkanols. Alkanol mixtures particularly preferred according to the present invention are those obtainable upon industrial hydrogenation of vegetable and animal fatty acids. The total quantity in the oxidizing agent composition (B) of at least one linear saturated alkanol having 12 to 30 carbon atoms is about 0.1 to about 10 wt %, preferably about 0.5 to about 7 wt %, and particularly preferably about 3 to about 5 wt %, based in each case on the total weight of the oxidizing agent composition (B).

Further preferred methods and kits of parts according to the present invention are characterized in that the composition (B) used according to the present invention contains:
about 1 to about 24 wt %, preferably about 4 to about 10 wt %, particularly preferably about 3 to about 6 wt % hydrogen peroxide (calculated as 100% $H_2O_2$), furthermore at least one cosmetic oil in a total quantity from about 12 to about 70 wt %, preferably about 14 to about 60 wt %, particularly preferably about 15 to about 52 wt %, and extraordinarily preferably about 17 to about 35 wt %,
furthermore at least one surfactant in a total quantity from about 0.1 to about 5 wt %, preferably about 0.5 to about 3 wt %, and particularly preferably about 1 to about 2 wt %, as well as
at least one linear saturated alkanol having about 12 to about 30 carbon atoms, in a total quantity from about 0.1 to about 10 wt %, preferably about 0.5 to about 7 wt %, and particularly preferably about 3 to about 5 wt %, where all "wt %" indications refer to the weight of composition (B).

Further methods preferred according to the present invention are characterized in that the post-treatment agent applied in method step b) contains at least one further hair-conditioning active substance that is selected from cationic surfactants that are preferably of the quaternary ammonium compound, esterquats, or amidoamines type, furthermore selected from cosmetic oils, linear C12 to C30 alkanols, in particular cetyl alcohol, stearyl alcohol, arachyl alcohol, behenyl alcohol, and mixtures thereof, and from amphoteric polymers and cationic polymers.

The composition (A) used in the method according to the present invention contains, as ingredients that are obligatory for coloring methods and optional for lightening methods, at least one oxidation dye precursor of the developer type and at least one oxidation dye precursor of the coupler type.

Oxidation dye precursors can be divided in terms of their reaction behavior into two categories: the so-called developer components and coupler components.

Coupler components alone do not produce any significant color in the context of oxidative coloring, but instead always require the presence of developer components. Developer components can form, with themselves, the actual dye.

The developer and coupler components are usually used in free form. In the case of substances having amino groups, however, it can be preferred to use them in salt form, in particular in the form of the hydrochlorides or hydrobromides or the sulfates.

It has been found, surprisingly, that hair coloring results with particularly good washing fastness could be achieved with the method according to the present invention using at least one oxidation dye precursor of the developer type and at least one oxidation dye precursor of the coupler type.

Particularly preferred developer components are selected from at least one compound of the group that is constituted from p-phenylenediamine, p-toluoylenediamine, 2-(2-hydroxyethyl)-p-phenylenediamine, 2-(1,2-dihydroxyethyl)-p-phenylenediamine, N,N-bis-(2-hydroxyethyl)-p-phenylenediamine, 2-methoxymethyl-p-phenylenediamine, N-(4-amino-3-methylphenyl)-N-[3-(1H-imidazol-1-yl)propyl] amine, N,N-bis-(2-hydroxyethyl)-N,N-bis-(4-aminophenyl)-1,3-diaminopropan-2-ol, bis-(2-hydroxy-5-aminophenyl)methane, 1,3-bis-(2,5-diaminophenoxy) propan-2-ol, N,N-bis-(4-aminophenyl)-1,4-diazacycloheptane, 1,10-bis-(2,5-diaminophenyl)-1,4,7,10-tetraoxadecane, p-aminophenol, 4-amino-3-methylphenol, 4-amino-2-aminomethylphenol, 4-amino-2-(1,2-dihydroxyethyl)phenol and 4-amino-2-(diethylaminomethyl)phenol, 4,5-diamino-1-(2-hydroxyethyl)pyrazole, 2,4,5,6-tetraminopyrimidine, 4-hydroxy-2,5,6-triaminopyrimidine, 2-hydroxy-4,5,6-triaminopyrimidine, the physiologically acceptable salts of these compounds, and mixtures of these developer components and developer component salts.

Very particularly preferred developer components are selected from 4,5-diamino-1-(2-hydroxyethyl)pyrazole, p-toluoylenediamine, 2-(2-hydroxyethyl)-p-phenylenediamine, 2-methoxymethyl-p-phenylenediamine, N-(4-amino-3-methylphenyl)-N-[3-(1H-imidazol-1-yl)propyl]amine,
and mixtures of these compounds as well as physiologically acceptable salts thereof. 4,5-Diamino-1-(2-hydroxyethyl) pyrazole and physiologically acceptable salts thereof are extraordinarily preferred.

The developer components are used preferably in a total quantity from about 0.01 to about 20 wt %, particularly preferably about 0.2 to about 10 wt %, and extraordinarily preferably about 0.6 to about 5 wt %, based in each case on the weight of composition (A).

The developer components are used preferably in a total quantity from about 0.005 to about 10 wt %, particularly preferably about 0.1 to about 5 wt %, and extraordinarily preferably about 0.3 to about 2.5 wt %, based in each case on the weight of the ready-to-use coloring agent.

The term "ready-to-use coloring and/or lightening agent" is understood for purposes of this Application as the mixture of composition (A) and composition (B). A suitable cosmetic carrier for composition (A) is, in particular, a cream base.

Coupler components for purposes of the invention allow at least one chemical residue of the coupler to be substituted with the oxidized form of the developer component, in which context a covalent bond forms between the coupler component and developer component. Couplers are preferably cyclic compounds that carry on the cycle at least two groups selected from (i) optionally substituted amino groups, and/or (ii) hydroxyl groups. If the cyclic compound is a six-membered ring (preferably aromatic), the aforesaid groups are then located preferably in the ortho or meta position with respect to one another.

Preferred methods according to the present invention are characterized in that the at least one oxidation dye precursor of the coupler type is selected from one of the following classes:
3-aminophenol (m-aminophenol) and/or derivatives thereof,
3-aminoaniline (m-diaminobenzene) and/or derivatives thereof,
2-aminoaniline (1,2-diaminobenzene; o-diaminobenzene) and/or derivatives thereof,
2-aminophenol (o-aminophenol) and/or derivatives thereof,
naphthalene derivatives having at least one hydroxy group,
di-resp. trihydroxybenzene and/or derivatives thereof,
pyridine derivatives,
pyrimidine derivatives, monohydroxyindole derivatives and/or monoaminoindole derivatives,
monohydroxyindoline derivatives and/or monoaminoindoline derivatives
pyrazolone derivatives such as e.g. 1-phenyl-3-methylpyrazol-5-one,
morpholine derivatives such as e.g. 6-hydroxybenzomorpholine or 6-aminobenzomorpholine,
quinoxaline derivatives such as e.g. 6-methyl-1,2,3,4-tetrahydroquinoxaline.

Mixtures of two or more compounds from one or more of these classes are likewise preferred according to the present invention in the context of this embodiment.

Additional coupler components particularly preferred according to the present invention are selected from 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)amino-2-methylphenol, 2,4-dichloro-3-aminophenol, 2-aminophenol, 3-phenylenediamine, 2-(2,4-diaminophenoxy)ethanol, 1,3-bis-(2,4-diaminophenoxy)propane, 1-methoxy-2-amino-4-(2'-hydroxyethylamino)benzene (=2-amino-4-hydroxyethylaminoanisole), 1,3-bis-(2,4-diaminophenyl)propane, 2,6-bis-(2'-hydroxyethylamino)-1-methylbenzene, 2-({3-[(2-hydroxyethyl)amino]-4-methoxy-5-methylphenyl}amino) ethanol, 2-({3-[(2-hydroxyethyl)amino]-2-methoxy-5-methylphenyl}amino)ethanol, 2-({3-[(2-hydroxyethyl)amino]-4,5-dimethylphenyl}amino) ethanol 2-[3-morpholin-4-ylphenyl)amino]ethanol, 3-amino-4-(2-methoxyethoxy)-5-methylphenylamine, 1-amino-3-bis-(2-hydroxyethyl)aminobenzene, resorcinol, 2-methylresorcinol, 4-chlororesorcinol, 1,2,4-trihydroxybenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazol-5-one, 1-naphthol, 1,5-dihydroxynaphthalene, 2,7-dihydroxynaphthalene, 1,7-dihydroxynaphthalene, 1,8-dihydroxynapthalene, 4-hydroxyindole, 6-hydroxyindole, 7-hydroxyindole, 4-hydroxyindoline, 6-hydroxyindoline, 7-hydroxyindoline, or mixtures of these compounds, or the physiologically acceptable salts of the aforesaid compounds.

Very particularly preferred in this context are 3-aminophenol, resorcinol, 2-methylresorcinol, 5-amino-2-methylphenol, 2-(2,4-diaminophenoxy)ethanol, 1,3-bis-(2,4-diaminophenoxy)propane, 1-methoxy-2-amino-4-(2'-hydroxyethylamino)benzene, 2-amino-3-hydroxypyridine, and 1-naphthol, as well as physiologically acceptable salts thereof and mixtures of the components recited.

The at least one coupler component is used preferably in a total quantity from about 0.01 to about 20 wt %, particularly preferably about 0.2 to about 10 wt %, and extraordinarily preferably about 0.6 to about 5 wt %, based in each case on the weight of composition (A).

The at least one coupler component is used preferably in a total quantity from about 0.005 to about 10 wt %, preferably about 0.1 to about 5 wt %, and extraordinarily preferably about 0.3 to about 2.5 wt %, based in each case on the weight of the ready-to-use oxidative coloring agent.

The following combinations of oxidation dye precursors of the developer type and of the coupler type are particularly preferred in the context of the present invention, where the amine compounds and the nitrogen heterocycles can also be present in the form of their physiologically acceptable salts:

p-toluoylenediamine/resorcinol;
p-toluoylenediamine/2-methylresorcinol;
p-toluoylenediamine/5-amino-2-methylphenol;
p-toluoylenediamine/3-aminophenol;
p-toluoylenediamine/2-(2,4-diaminophenoxy)ethanol;
p-toluoylenediamine/1,3-bis-(2,4-diaminophenoxy)propane;
p-toluoylenediamine/1-methoxy-2-amino-4-(2-hydroxyethylamino)benzene;
p-toluoylenediamine/2-amino-3-hydroxypyridine;
p-toluoylenediamine/1-naphthol;
2-(2-hydroxyethyl)-p-phenylenediamine/resorcinol;
2-(2-hydroxyethyl)-p-phenylenediamine/2-methylresorcinol;
2-(2-hydroxyethyl)-p-phenylenediamine/5-amino-2-methylphenol;
2-(2-hydroxyethyl)-p-phenylenediamine/3-aminophenol;
2-(2-hydroxyethyl)-p-phenylenediamine/2-(2,4-diaminophenoxy)ethanol;
2-(2-hydroxyethyl)-p-phenylenediamine/1,3-bis-(2,4-diaminophenoxy)propane;
2-(2-hydroxyethyl)-p-phenylenediamine/1-methoxy-2-amino-4-(2-hydroxyethylamino)benzene;
2-(2-hydroxyethyl)-p-phenylenediamine/2-amino-3-hydroxypyridine;
2-(2-hydroxyethyl)-p-phenylenediamine/1-naphthol;
2-methoxymethyl-p-phenylenediamine/resorcinol;
2-methoxymethyl-p-phenylenediamine/2-methylresorcinol;
2-methoxymethyl-p-phenylenediamine/5-amino-2-methylphenol;
2-methoxymethyl-p-phenylenediamine/3-aminophenol;
2-methoxymethyl-p-phenylenediamine/2-(2,4-diaminophenoxy)ethanol;
2-methoxymethyl-p-phenylenediamine/1,3-bis-(2,4-diaminophenoxy)propane;
2-methoxymethyl-p-phenylenediamine/1-methoxy-2-amino-4-(2-hydroxyethylamino)benzene;
2-methoxymethyl-p-phenylenediamine/2-amino-3-hydroxypyridine;
2-methoxymethyl-p-phenylenediamine/1-naphthol;
N-(4-amino-3-methylphenyl)-N-[3-(1H-imidazol-1-yl)propyl]amine/resorcinol;
N-(4-amino-3-methylphenyl)-N-[3-(1H-imidazol-1-yl)propyl]amine/2-methylresorcinol;
N-(4-amino-3-methylphenyl)-N-[3-(1H-imidazol-1-yl)propyl]amine/5-amino-2-methylphenol;
N-(4-amino-3-methylphenyl)-N-[3-(1H-imidazol-1-yl)propyl]amine/3-aminophenol;
N-(4-amino-3-methylphenyl)-N-[3-(1H-imidazol-1-yl)propyl]amine diaminophenoxy)ethanol;
N-(4-amino-3-methylphenyl)-N-[3-(1H-imidazol-1-yl)propyl]amine/1,3-bis-(2,4-diaminophenoxy)propane;
N-(4-amino-3-methylphenyl)-N-[3-(1H-imidazol-1-yl)propyl]amine/1-methoxy-2-amino-4-(2-hydroxyethylamino)benzene;
N-(4-amino-3-methylphenyl)-N-[3-(1H-imidazol-1-yl)propyl]amine/2-amino-3-hydroxypyridine;
N-(4-amino-3-methylphenyl)-N-[3-(1H-imidazol-1-yl)propyl]amine/1-naphthol;
4,5-diamino-1-(2-hydroxyethyl)pyrazole/resorcinol;
4,5-diamino-1-(2-hydroxyethyl)pyrazole/2-methylresorcinol;
4,5-diamino-1-(2-hydroxyethyl)pyrazole/5-amino-2-methylphenol;

4,5-diamino-1-(2-hydroxyethyl)pyrazole/3-aminophenol;
4,5-diamino-1-(2-hydroxyethyl)pyrazole/2-(2,4-diaminophenoxy)ethanol;
4,5-diamino-1-(2-hydroxyethyl)pyrazole/1,3-bis-(2,4-diaminophenoxy)propane;
4,5-diamino-1-(2-hydroxyethyl)pyrazole 1-methoxy-2-amino-4-(2-hydroxyethylamino)benzene;
4,5-diamino-1-(2-hydroxyethyl)pyrazole/2-amino-3-hydroxypyridine;
4,5-diamino-1-(2-hydroxyethyl)pyrazole/1-naphthol.

The combinations 4,5-diamino-1-(2-hydroxyethyl)pyrazole/3-aminophenol and p-toluoylenediamine/3-aminophenol are particularly preferred according to the present invention. The combination 4,5-diamino-1-(2-hydroxyethyl)pyrazole/3-aminophenol is extraordinarily preferred, in particular in terms of improving washing fastness.

In order to achieve balanced and subtle toning, it is preferred according to the present invention if further color-imparting components are contained in the coloring agent that is used in the method according to the present invention.

In a further embodiment, the agents used in step b) of this variant of the method according to the present invention can additionally contain at least one substantive dye. These are dyes that absorb directly onto the hair and do not require an oxidizing process for formation of the color. Substantive dyes are usually nitrophenylenediamines, nitroaminophenols, azo dyes, anthraquinones, or indophenols.

A further preferred method according to the present invention is characterized in that the coloring and/or lightening agent applied in step b) is rinsed off the fibers after a period from about 5 to about 60 minutes, preferably about 15 to about 50 minutes, particularly preferably about 30 to about 45 minutes.

The coloring agent used in the method according to the present invention in step b) is produced from a two-component agent, where one component, namely composition (A), contains at least one alkalizing agent, at least one acylpyridinium derivative of formula (Acylpyr-I), and optionally the oxidation dye precursors and/or substantive dyes, and the other component, namely composition (B), contains the oxidizing agent or agents. The ready-to-use coloring and/or lightening agent for step b) is then produced by mixing the two components directly before the application step b). A separation into multi-component systems is advisable in particular when incompatibilities of the ingredients are expected or are a concern.

A further subject of the present Application is therefore a multi-component packaging unit (kit of parts) encompassing
(i) a first container (C1) having an agent containing at least one 4-morpholinomethyl-substituted silicone of formula (V),

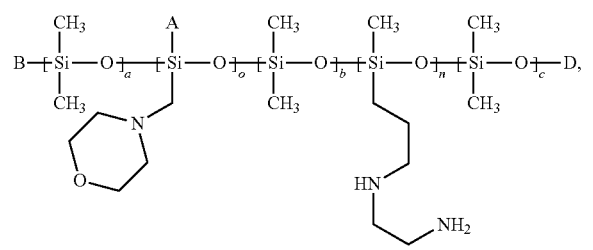

(V)

in which
A denotes a structural unit (I), (II), or (III) bound via-0

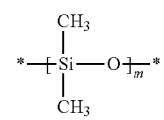

(I)

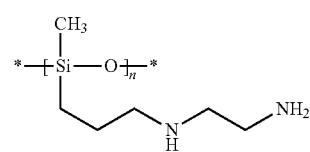

(II)

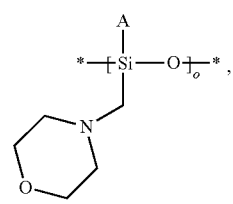

(III)

or an oligomeric or polymeric residue bound via —O— containing structural units of formulas (I), (II), or (III), or half of an oxygen atom connecting to a structural unit (III), or denotes —OH,
* denotes a bond to one of the structural units (I), (II), or (III), or denotes a terminal group B (Si-bound) or D (O-bound),
B denotes an —OH, —O—Si(CH$_3$)$_3$, —O—Si(CH$_3$)$_2$OH, —O—Si(CH$_3$)$_2$OCH$_3$ group,
D denotes an —H, —Si(CH$_3$)$_3$, —Si(CH$_3$)$_2$OH, —Si(CH$_3$)$_2$OCH$_3$ group,
a, b, and c denote integers from 0 to 990, with the provision that a+b+c>0,
m, n, and o denote integers from 1 to 990,
furthermore
(ii) a second container (C2) having a composition (A) containing at least one alkalizing agent,
(iii) and furthermore a third container (C3) having a composition (B) containing, in a cosmetic carrier, at least one oxidizing agent and at least one acylpyridinium derivative of formula (Acylpyr-I), (Acylpyr-I), in which
R1 denotes a C$_1$ to C$_6$ alkyl group, a C$_2$ to C$_6$ alkenyl group, a C$_2$ to C$_6$ hydroxyalkyl group, a C$_1$ to C$_6$ alkoxy-C$_2$ to C$_6$ alkyl group, a carboxy C$_2$ to C$_6$ alkyl group, an aryl C$_1$ to $C_6$ alkyl group, a heteroaryl $C_1$ to $C_6$ alkyl group, an aryl group, or a heteroaryl group, R2, R3, and R4 mutually independently in each case denote hydrogen, a $C_1$ to $C_6$ alkyl group, a halogen atom, or a $C_1$ to $C_6$ acyl group, with the provision that at least one of the residues R2, R3, and R4 denotes a $C_1$ to $C_6$ acyl group, and $X^-$ denotes a physiologically acceptable anion.

The statements made above regarding preferred embodiments of the method according to the present invention also apply mutatis mutandis to the multi-component packaging units according to the present invention.

EXEMPLIFYING EMBODIMENTS

Producing the Coloring Agent Applied in Method Step a)

TABLE 1

| Composition (A): color cream (quantities indicated in wt %) | |
|---|---|
| Ingredient | (A)-1 |
| 1-Hydroxyethyl-4,5-diaminopyrazole sulfate | 1.5 |
| Toluene-2,5-diamine sulfate | — |
| 3-Aminophenol | 0.6 |
| Resorcinol | — |
| 2-Amino-4-hydroxyethylaminoanisole sulfate (1-methoxy-2-amino-4-(2'-hydroxyethylamino)benzene sulfate) | — |
| 4-Amino-2-Hydroxytoluene | 0.3 |
| 4-Amino-m-Cresol | 0.18 |
| Cetearyl alcohol | 14 |
| Glyceryl stearate | 1.4 |
| Ammonium hydroxide | 3.4 |
| Ceteareth-20 | 3.5 |
| Octyldodecanol | 1 |
| Sodium laureth sulfate (3 EO) | 0.5 |
| 1,3-Butylene glycol | 3.5 |
| Sodium cetearyl sulfate | 1.0 |
| Monoethanolamine | 0.6 |
| Oleic acid | 0.1 |
| Perfume | 0.5 |
| Potassium stearate | 0.5 |
| Sodium sulfite | 0.2 |
| Tetrasodium EDTA | 0.3 |
| Carbomer | 0.3 |
| Polyquaternium-39 (ex Merquat 3330) | 0.05 |
| Potassium hydroxide | 0.08 |
| Ascorbic acid | 0.02 |
| Linoleamidopropyl PG-Dimonium Chloride Phosphate | 0.1 |
| Sodium sulfate | 0.1 |
| Citric acid | 0.002 |
| CI 77891 (Titanium dioxide) | 0.3 |
| Water | to 100 |

The composition (A)-1 listed above was mixed at a 1:1 weight ratio with the composition (B)-1 presented in Table 2 (=Oxidizing agent composition (B)) to yield a ready-to-use coloring agent. The ready-to-use coloring agent was then applied onto untreated test skeins, specifically at a rate of 4 g coloring agent per gram of hair for the combing tests, and 5 g coloring agent per gram of hair for the washing fastness test.

The coloring agent remained on the skeins for 30 minutes in each case. The skeins were then rinsed out for 2 minutes using warm (32° C.) tap water at a flow rate of 0.5 liter per minute.

TABLE 2

| Developer dispersion used (quantities indicated in wt %) | |
|---|---|
| Ingredients | (B)-1 |
| Cetearyl Alcohol | 4.0 |
| Dipicolinic acid | 0.1 |
| Disodium Pyrophosphate | 0.1 |
| Potassium hydroxide | 0.1 |
| 1,2-Propylene glycol | 1.0 |
| 1-Hydroxyethane-1,1-Diphosphonic Acid (Etidronic Acid) | 0.1 |
| Paraffinum Liquidum | 0.5 |
| Steartrimonium Chloride | 0.5 |
| Ceteareth-20 | 1.0 |
| $H_2O_2$ (active matter) | 6.0 |
| Water | to 100 |

The effectiveness of the post-treatment according to the present invention, in terms of reducing hair damage to hair skeins that had been colored and rinsed out according to the protocol presented above, was checked with the aid of several test series. All test series represent a method according to the present invention for oxidative coloring with a post-treatment using the silicone of formula (V).

Test series 1:

The colored and rinsed-out skeins were treated for two minutes with the conditioner presented in Table 3, and rinsed.

Test series 2:

The colored and rinsed-out skeins were immersed for two minutes into an aqueous emulsion of a 4-morpholinomethyl-substituted silicone of formula (V) that contained 0.01 wt % 4-morpholinomethyl-substituted silicone(s) of formula (V) and 0.005 wt % branched Trideceth-5, furthermore 0.006 wt % glycerol, and water to 100 wt %. The skeins were then removed from the immersion bath and rinsed.

Test series 3:

The colored and rinsed-out skeins were cleaned using the shampoo presented in Table 4. They were then treated for two minutes with the conditioner presented in Table 3, and rinsed.

Test series 4:

The colored and rinsed-out skeins were cleaned using the shampoo presented in Table 4, and then immersed for two minutes into an aqueous emulsion of a 4-morpholinomethyl-substituted silicone of formula (V) that contained 0.01 wt % 4-morpholinomethyl-substituted silicone(s) of formula (V) and 0.005 wt % branched Trideceth-5, furthermore 0.006 wt % glycerol, and water to 100 wt %. The skeins were then removed from the immersion bath and rinsed.

At the completion of all four test series, the skeins were then combed three times before the actual combability measurements (10 comb strokes each on 20 skeins) were carried out.

TABLE 3

| Conditioner (quantities indicated in wt %) | |
|---|---|
| Glyceryl stearate | 0.8 |
| Distearoylethyl Hydroxyethylmonium Methosulfate | 0.5 |
| Cetearyl Alcohol | 5.5 |
| Quaternium-87 | 3.0 |
| Ceteareth-20 | 0.3 |
| Isopropyl palmitate | 1.0 |
| Stearamidopropyl Dimethylamine | 0.4 |
| Lactic acid | 0.4 |
| Methylparaben | 0.3 |
| Keratin hydrolysate | 0.05 |

TABLE 3-continued

Conditioner (quantities indicated in wt %)

| | |
|---|---|
| Phenoxyethanol | 0.1 |
| Wacker Belsil ADM 8301E | 0.20 |
| Perfume | 0.5 |
| 1,2-Propylene glycol | 3 |
| Water | to 100 |

TABLE 4

Shampoo (quantities indicated in wt %)

| | |
|---|---|
| Sodium Laureth Sulfate | 9.0 |
| Sodium Hydroxide | 0.15 |
| Citric Acid | 0.4 |
| Disodium Cocoamphodiacetate | 1.0 |
| Sodium Benzoate | 0.5 |
| Glycol Distearate | 1.0 |
| Cocamidopropyl Betaine | 0.5 |
| Laureth-4 | 0.5 |
| Hydrolyzed Keratin | 0.04 |
| Perfume | 0.3 |
| PEG-40 Hydrogenated Castor Oil | 0.1 |
| PEG-7 Glyceryl Cocoate | 0.3 |
| Hydrogenated Castor Oil | 0.1 |
| Cocamide MEA | 0.7 |
| Polyquaternium-10 | 0.1 |
| Cocamidopropyl Betaine | 2.0 |
| Water | to 100 |

TABLE 5

Wet combability; combing work (mJ)

| | Combing work (mJ) |
|---|---|
| untreated | 633 |
| Test series 1 | 238 |
| Test series 2 | 523 |
| Test series 3 | 330 |
| Test series 4 | 461 |

TABLE 6

Split count after 20,000 comb strokes (proportion as %)

| | Split count (%) |
|---|---|
| Test series 1 | 8.8 |
| Test series 2 | 5.3 |
| Test series 3 | 7.1 |
| Test series 4 | 3.7 |

TABLE 7

Hair breakage after 20,000 comb strokes (proportion as %)

| | (%) |
|---|---|
| Test series 1 | 6.1 |
| Test series 2 | 3.0 |

TABLE 7-continued

Hair breakage after 20,000 comb strokes (proportion as %)

| | (%) |
|---|---|
| Test series 3 | 5.8 |
| Test series 4 | 2.8 |

TABLE 8

Washing fastness after 36 washing cycles (L a b color difference ΔE)

| | |
|---|---|
| untreated | 6.2 |
| Test series 1 | 5.7 |
| Test series 2 | 5.5 |
| Test series 3 | 4.9 |
| Test series 4 | 5.2 |

$\Delta E = E_{before\ washing} - E_{after\ washing}$

As shown by the data presented in Tables 5 to 8, with all methods according to the present invention it is possible to reduce the hair damage caused by oxidative coloring and to improve the washing fastness of the color.

The invention claimed is:

1. A method for oxidative lightening and/or coloring of keratinic fibers, wherein a) a coloring and/or lightening agent is applied onto the keratinic fibers, which agent is obtained by mixing a composition (A) that contains at least one alkalizing agent with a composition (B) that contains, in a cosmetic carrier, at least one oxidizing agent, b) subsequently, within a time span from about one second to about 24 hours after step a), a post-treatment agent that contains at least one 4-morpholinomethyl-substituted silicone of formula (V),

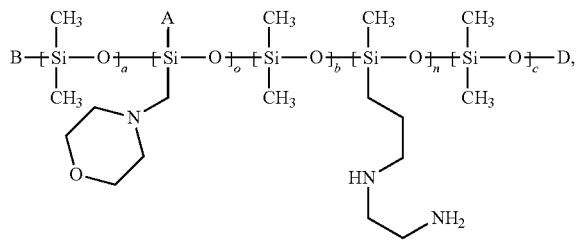

in which

A denotes a structural unit (I), (II), or (III) bound via-0

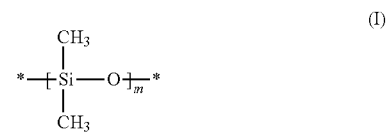

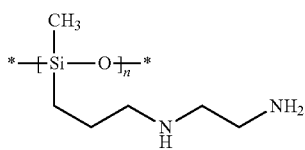
(II)

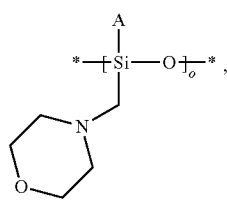
(III)

or an oligomeric or polymeric residue bound via —O— containing structural units of formulas (I), (II), or (III), or half of an oxygen atom connecting to a structural unit (III), or denotes —OH,
* denotes a bond to one of the structural units (I), (II), or (III), or denotes a terminal group B (Si-bound) or D (O-bound),
B denotes an —OH, —O—Si(CH$_3$)$_3$, —O—Si(CH$_3$)$_2$OH, —O—Si(CH$_3$)$_2$OCH$_3$ group,
D denotes an —H, —Si(CH$_3$)$_3$, —Si(CH$_3$)$_2$OH, —Si(CH$_3$)$_2$OCH$_3$ group,
a, b, and c denote integers from 0 to 990, with the provision that a+b+c>0,
m, n, and o denote integers from 1 to 990,
is applied onto the keratinic fibers, in particular onto the hair.

2. The method according to claim 1, wherein the post-treatment agent used in step b) contains at least one 4-morpholinomethyl-substituted silicone of formula (V) in which $$m>(n+o) \text{ resp. } (a+b+c)>(n+o).$$

3. The method according to claim 1, wherein the post-treatment agent used in step b) contains, based on its weight, 4-morpholinomethyl-substituted silicone(s) in a total quantity from about 0.001 to about 5 wt %, based on the total weight of the post-treatment agent.

4. The method according to claim 1, wherein the post-treatment agent used in step b) contains, based on its weight, at least one 4-morpholinomethyl-substituted silicone of formula (V) that respectively comprises at least one of the structural units of formulas (I), (II), and (III), in a total quantity from about 0.001 to about 5 wt %, based on the total weight of the post-treatment agent.

5. The method according to claim 1, wherein the post-treatment agent used in step b) contains hydroxy-terminated 4-morpholinomethyl-substituted silicone(s) in which the molar ratio of hydroxy to alkoxy is in the range from about 0.2:1 to about 0.4:1.

6. The method according to claim 1, wherein the weight-average molar mass of the 4-morpholinomethyl-substituted silicone of formula (V) used in step b) is in the range from about 2,000 to about 1,000,000 gmol$^{-1}$.

7. The method according to claim 1, wherein the 4-morpholinomethyl-substituted silicone of formula (V) used in step b) is present in the form of an oil-in-water emulsion in which the number-average size of the silicone particles in the emulsion is in the range from about 3 to about 500 nm.

8. The method according to claim 1, wherein the post-treatment agent applied in method step b) contains at least one further hair-conditioning active substance that is selected from cationic surfactants that are of the quaternary ammonium compound, esterquats, or amidoamines type, from cosmetic oils, from linear C12 to C30 alkanols, from amphoteric polymers and from cationic polymers.

9. The method according to claim 1, wherein composition (B) contains at least one cosmetic oil in a total quantity from about 10 to about 80 wt %, based on the weight of composition (B).

10. The method according to claim 1, wherein in method step a) the coloring agent is applied onto the keratinic fibers, which agent is obtained by mixing the composition (A), which contains the at least one alkalizing agent, at least one oxidation dye precursor of the developer type, and at least one oxidation dye precursor of the coupler type, with the composition (B).

11. The method according to claim 1, wherein the method for oxidative lightening and/or coloring of keratinic fibers is for oxidative lightening and/or coloring of human hair.

* * * * *